(12) United States Patent
Tarutani et al.

(10) Patent No.: US 10,087,262 B2
(45) Date of Patent: Oct. 2, 2018

(54) ETHYLENE POLYMER, STRETCH-MOLDED PRODUCT OBTAINED BY STRETCHING THE SAME, AND METHOD FOR PRODUCING ETHYLENE POLYMER

(71) Applicant: Asahi Kasei Kabushiki Kaisha, Tokyo (JP)

(72) Inventors: Atsuyoshi Tarutani, Tokyo (JP); Kazuyoshi Kataoka, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/516,261

(22) PCT Filed: Oct. 5, 2015

(86) PCT No.: PCT/JP2015/078236
§ 371 (c)(1),
(2) Date: Mar. 31, 2017

(87) PCT Pub. No.: WO2016/052751
PCT Pub. Date: Apr. 7, 2016

(65) Prior Publication Data
US 2017/0298156 A1    Oct. 19, 2017

(30) Foreign Application Priority Data
Oct. 3, 2014  (JP) ................. 2014-205180

(51) Int. Cl.
| | | |
|---|---|---|
| C08F 10/02 | (2006.01) | |
| C08F 4/6592 | (2006.01) | |
| D01F 6/04 | (2006.01) | |
| C08F 4/42 | (2006.01) | |
| G01N 25/48 | (2006.01) | |
| G01N 11/14 | (2006.01) | |
| B29C 49/08 | (2006.01) | |

(52) U.S. Cl.
CPC .............. *C08F 10/02* (2013.01); *B29C 49/08* (2013.01); *C08F 4/42* (2013.01); *G01N 11/142* (2013.01); *G01N 25/4866* (2013.01); *C08F 2500/01* (2013.01)

(58) Field of Classification Search
CPC ...... C08F 10/02; C08F 110/00; C08F 110/02; C08F 210/00; C08F 210/002; C08F 4/6592; D01F 6/04
See application file for complete search history.

(56) References Cited

U.S. PATENT DOCUMENTS

| | | | |
|---|---|---|---|
| 4,422,993 A | 12/1983 | Smith et al. | |
| 5,387,568 A | 2/1995 | Ewen et al. | |
| 2002/0012793 A1* | 1/2002 | Tajima | C08F 110/02 428/364 |
| 2008/0090081 A1 | 4/2008 | Matsumoto et al. | |
| 2010/0317813 A1 | 12/2010 | Tait et al. | |
| 2011/0256402 A1 | 10/2011 | Sugiyama et al. | |
| 2013/0260624 A1 | 10/2013 | Rastogi et al. | |
| 2015/0249242 A1* | 9/2015 | Kamo | H01M 2/162 526/194 |
| 2016/0137760 A1* | 5/2016 | Kuwata | C08F 10/02 428/402 |

FOREIGN PATENT DOCUMENTS

| | | |
|---|---|---|
| CN | 101616937 A | 12/2009 |
| JP | S56-015408 A | 2/1981 |
| JP | H07-156173 A | 6/1995 |
| JP | 2943310 B2 | 8/1999 |
| JP | 2001-278909 A | 10/2001 |
| JP | 2001-278911 A | 10/2001 |
| JP | 2003-226711 A | 8/2003 |
| JP | 2003-226712 A | 8/2003 |
| JP | 2014-504311 A | 2/2014 |
| WO | 2008/013144 A1 | 1/2008 |
| WO | 2010/074073 A | 7/2010 |

OTHER PUBLICATIONS

Thomas, J.M., et al. Nature vol. 378(9) pp. 159-162 (Nov. 1995).*
International Search Report issued in corresponding International Patent Application No. PCT/JP2015/078236 dated Dec. 8, 2015.
Kageyama et al., "Extrusion Polymerization: Catalyzed Synthesis of Crystalline Linear Polyethylene Nanofibers Within a Mesoporous Silica," Science, 285: 2113-2115 (1999).
International Preliminary Report on Patentability and Written Opinion issued in corresponding International Patent Application No. PCT/JP2015/078236 dated Apr. 4, 2017.

* cited by examiner

Primary Examiner — Irina Sopjia Zemel
Assistant Examiner — Jeffrey S Lenihan
(74) Attorney, Agent, or Firm — Morgan, Lewis & Bockius LLP

(57) ABSTRACT

Disclosed is an ethylene polymer having a viscosity-average molecular weight (Mv) of 3,000,000 or more and 15,000,000 or less.

16 Claims, No Drawings

ETHYLENE POLYMER, STRETCH-MOLDED PRODUCT OBTAINED BY STRETCHING THE SAME, AND METHOD FOR PRODUCING ETHYLENE POLYMER

TECHNICAL FIELD

The present invention relates to an ethylene polymer, a stretch-molded product obtained by stretching the same, and a method for producing an ethylene polymer.

BACKGROUND ART

High-molecular-weight polyethylene is a characteristic engineering plastic, which is excellent in terms of impact resistance and abrasion resistance, and has self-lubricating property, and thus, such high-molecular-weight polyethylene has been used in various fields. Since this high-molecular-weight polyethylene has a much higher molecular weight in comparison to commonly used polyethylene, it is anticipated that a molded product having high strength and high elasticity can be obtained by a high degree of orientation of the high-molecular-weight polyethylene. As such, various studies have been conducted to obtain such highly oriented high-molecular-weight polyethylene.

Patent Literature 1 discloses a technique regarding, what is called, a gel spinning process, in which gel-state fibers obtained by dissolving high-molecular-weight polyethylene in a solvent are stretched at a high ratio. Polyethylene fibers obtained by the gel spinning process have extremely high strength and high modulus of elasticity, and further, the fibers have been known to be extremely excellent in impact resistance. However, these polyethylene fibers have been problematic in terms of the aspects of environment, cost and production rate, since a large amount of solvent is used in the gel spinning process, a step of dissolving high-molecular-weight polyethylene in a solvent and a step of drying a product after completion of stretch molding are required, and the like.

On the other hand, a molding method of compressing high-molecular-weight ethylene polymer particles at a temperature lower than the melting point and then stretching them, namely, a so-called solid-phase stretching method, has also been developed. The solid-phase stretching method is considered to be superior to the gel spinning process in terms of a processing process in that no solvents are used. However, in the solid-phase stretching method, since polymer particles are compressed, rolled and stretched at the melting point or lower, insufficient pressure bonding of polymer particles, insufficient stretching caused by the entanglement of polymer chains, and the like have occurred, and thus, a problem of this method is that molding processing is very difficult.

In contrast, Patent Literatures 2 and 3 disclose a technique of achieving high molecular weight, high crystallinity, and regulation of particle surface structure, particle diameter and molecular weight distribution, so as to improve the processability of an ethylene polymer and the mechanical strength of a molded product. However, even in the case of a solid-phase stretch-molded product obtained from such an ethylene polymer, the mechanical strength of the solid-phase stretch-molded product has not yet exceeded the mechanical strength of a stretch-molded product obtained by the gel spinning process.

As a method of regulating a higher-order structure to obtain an ethylene polymer suitable for solid-phase stretching, and in particular, as a method of reducing entanglement in polymers, a method of suppressing the interference of polymer molecular chains in polymerization with other polymer molecular chains has been considered. Patent Literature 4 and Non Patent Literature 1 disclose a technique of utilizing, as polymerization fields, the pores of mesoporous silica used as a polymerization catalyst, to suppress free movements of molecules during the growth of the polymer, so as to suppress the entanglement of molecular chains and control crystallinity and the morphology of the obtained polymer.

CITATION LIST

Patent Literature

Patent Literature 1: Japanese Patent Laid-Open No. 56-15408
Patent Literature 2: International Publication No. WO 2008/013144
Patent Literature 3: National Publication of International Patent Application No. 2014-504311
Patent Literature 4: Japanese Patent Laid-Open No. 2001-278909

Non Patent Literature

Non Patent Literature 1: Science 285, 2113 (1999)

SUMMARY OF INVENTION

Technical Problem

However, Patent Literature 4 does not describe the achievement of both a high-molecular-weight polymer and high crystallinity. In addition, although Non Patent Literature 1 describes such a high-molecular-weight polymer and high crystallinity, the crystal structure consists of hexagonal extended chain crystals. It is considered that such an extended chain structure is not suitable for processing such as the pressure bonding of polymer particles or stretching.

The present invention has been made to solve these problems, and it is an object of the present invention to provide an ethylene polymer, which is excellent in terms of stretch processability, enables the improvement of productivity by high-speed stretch processing, and can be used to produce molded products excellent in terms of strength, dimensional stability, adhesion and thickness uniformity, and a stretch-molded product comprising the same, and a method for producing the ethylene polymer.

Solution to Problem

As a result of intensive studies directed toward achieving the aforementioned object, the present inventors have found that an ethylene polymer, which has a specific molecular weight and a specific quantity of heat of fusion, and also has a large change rate in 200/110 plane orientation index analyzed from X-ray diffraction, when the ethylene polymer processed under specific conditions is compared with the unprocessed ethylene polymer, can achieve the aforementioned object, thereby completing the present invention.

Specifically, the present invention is as follows.

<1> An ethylene polymer having a viscosity-average molecular weight (Mv) of 3,000,000 or more and 15,000,000 or less, wherein the quantity of heat of fusion ΔH measured by differential scanning calorimetry, of the ethylene polymer to which heat history at 110° C. for 6 hours has been given under a reduced pressure environment of 0.1 to 0.5 kPa, is 230 J/g or more and 293 J/g or less, and the plane orientation index ratio (b)/(a), between 200/110 plane orientation index (a) in an unprocessed ethylene polymer and 200/110 plane orientation index (b) in a sheet which has been subjected to press processing and rolling processing under the following conditions (1) to (3), is 7 or more:

(1) 3 g of the ethylene polymer is pressed using a press molding machine at 130° C. at 11 MPa for 10 minutes, (2) the resultant is cooled at 25° C. for 10 minutes, while maintaining the pressure at 11 MPa, and (3) the obtained press sheet is heated at 140° C. for 3 minutes, and the resulting sheet is then compressed using a rolling mill having a temperature of 130° C. and a feeding rate of the roll of 1 m/min, to result in a stretch ratio of 6.

<2> The ethylene polymer according to the above <1>, wherein the plane orientation index ratio (b)/(a) is 16 or more.

<3> The ethylene polymer according to the above <1> or <2>, wherein the difference in melting point ($Tm_{1b} - Tm_{1a}$), between the melting point ($Tm_{1a}$) of the unprocessed ethylene polymer by differential scanning calorimetry and the melting point ($Tm_{1b}$) of the sheet subjected to press processing and rolling processing by differential scanning calorimetry under the above conditions (1) to (3), is 3.0° C. or more.

<4> A stretch-molded product obtained by the stretch molding of the ethylene polymer according to any one of the above <1> to <3>, wherein the stretch-molded product has a tensile strength of 3.0 GPa or more.

<5> A method for producing the ethylene polymer according to any one of the above <1> to <3>, which comprises a step of performing polymerization using a mixed solvent comprising 50% by mass or more of an aliphatic hydrocarbon.

<6> A method for producing the ethylene polymer according to any one of the above <1> to <3>, which comprises a step of performing polymerization using an olefin polymerization catalyst comprising (A) a transition metal compound, and (C) at least one compound used as a co-catalyst which is selected from among (C-1) an organic metal compound, (C-2) an organic aluminum oxy compound, and (C-3) a compound reacting with (A) the transition metal compound to form an ion pair.

<7> A method for producing the ethylene polymer according to any one of the above <1> to <3>, which comprises a step of allowing (A) a transition metal compound to come into contact with (B) a mesoporous structure compound to obtain a transition metal-containing mesoporous structure compound, and then using (C) at least one compound used as a co-catalyst which is selected from among (C-1) an organic metal compound, (C-2) an organic aluminum oxy compound, and (C-3) a compound reacting with (A) the transition metal compound to form an ion pair, to perform polymerization using an olefin polymerization catalyst comprising the transition metal-containing mesoporous structure compound and the co-catalyst.

<8> A method for producing the ethylene polymer according to any one of the above <1> to <3>, which comprises a step of allowing (A) a transition metal compound to come into contact with (B) a mesoporous structure compound, then allowing the mixture to come into contact with a substance having the function of modifying (A) the transition metal compound to obtain a transition metal-containing mesoporous structure compound, and then using (C) at least one compound used as a co-catalyst which is selected from among (C-1) an organic metal compound, (C-2) an organic aluminum oxy compound, and (C-3) a compound reacting with (A) the transition metal compound to form an ion pair, to perform polymerization using an olefin polymerization catalyst comprising the transition metal-containing mesoporous structure compound and the co-catalyst.

<9> A method for producing the ethylene polymer according to any one of the above <1> to <3>, which comprises a step of allowing (A) a transition metal compound to come into contact with (B) a mesoporous structure compound, in which reactive points on the outer surfaces of mesopores have been inactivated, to obtain a transition metal-containing mesoporous structure compound, and then using (C) at least one compound used as a co-catalyst which is selected from among (C-1) an organic metal compound, (C-2) an organic aluminum oxy compound, and (C-3) a compound reacting with (A) the transition metal compound to form an ion pair, to perform polymerization using an olefin polymerization catalyst comprising the transition metal-containing mesoporous structure compound and the co-catalyst.

<10> The method for producing an ethylene polymer according to any one of the above <7> to <9>, wherein the pore size of (B) the mesoporous structure compound is 1.5 nm or more and 10 nm or less.

<11> A method for producing a stretch-molded product, comprising at least a step of step of compressing and a step of step of stretching, wherein the ethylene polymer according to any one of the above <1> to <3> is subjected to the step of step of compressing and the step of step of stretching under conditions that do not increase the temperature above the melting point of the ethylene polymer at any time point during processing in the step of step of compressing and the step of step of stretching.

<12> The method for producing a stretch-molded product according to the above <11>, wherein the tensile strength of the obtained stretch-molded product is 3.0 GPa or more.

Advantageous Effects of Invention

According to the present invention, an ethylene polymer, which is excellent in terms of stretch processability, enables the improvement of productivity by high-speed stretch processing, and can be used to produce molded products excellent in terms of strength, dimensional stability, adhesion and thickness uniformity, and a stretch-molded product comprising the same, and a method for producing the ethylene polymer, can be provided.

DESCRIPTION OF EMBODIMENTS

Hereinafter, the mode for carrying out the present invention (hereinafter referred to as "the present embodiment") will be described in detail. It is to be noted that the present invention is not limited to the following embodiments, and that it can be modified, as appropriate, and can be carried out within the range of the gist thereof.

[Ethylene Polymer]

The "ethylene polymer" of the present embodiment means a substantial ethylene homopolymer, in which 99.5 mol % or more of, and preferably 99.8 mol % or more of structural units consist of ethylene units. It is to be noted that it is possible to add very small quantities of copolymer components, such as α-olefin, to the ethylene polymer to introduce branches therein, for the purpose of improving polymerization speed or improving the creep properties of finally obtained fibers. However, if the amount of such copolymer components is too large, branches become starting points for the entanglement of molecular chains when the ethylene polymer is stretched at high orientation, so that it would cause the inhibition of stretchability. Since the ethylene polymer of the present embodiment has an extremely high molecular weight and also has a high quantity of heat of fusion, a highly strong molded product can be obtained using the present ethylene polymer according to a molding method involving the solid-phase stretching method. Moreover, since the present ethylene polymer has a low degree of entanglement of molecular chains and also has high orientation in the stretching direction, it suppresses ununiformity during the stretching process, and can realize suppression of the thickness unevenness of stretch processed products and the improvement of dimensional stability.

The type of the copolymer component is not particularly limited, and examples of the copolymer include α-olefin and a vinyl compound.

The type of the α-olefin is not particularly limited, and for example, it is α-olefin containing 3 to 20 carbon atoms. Specific examples of such α-olefin containing 3 to 20 carbon atoms include propylene, 1-butene, 4-methyl-1-pentene, 1-hexene, 1-octene, 1-nonene, 1-decene, 1-undecene, 1-dodecene, 1-tridecene, and 1-tetradecene. Among these compounds, from the viewpoint of the heat resistance and strength of molded products including films and fibers as representative examples, propylene and 1-butene are preferable.

Moreover, examples of the vinyl compound include a styrene derivative, (meth)acrylic acid ester, vinyl alkyl ether, and carboxylic acid vinyl ester.

The copolymer component may be used as a single type alone, or may also be used in combination of two or more types.

When the ethylene polymer is a copolymer, the amount of other comonomers in the copolymer can be confirmed by an NMR method.

[Viscosity-average Molecular Weight (Mv)]

The ethylene polymer of the present embodiment has a viscosity-average molecular weight (Mv) of 3,000,000 or more and 15,000,000 or less.

Since the present ethylene polymer has a viscosity-average molecular weight (Mv) of 3,000,000 or more, a molded product excellent in terms of strength can be obtained. On the other hand, since the present ethylene polymer has a viscosity-average molecular weight (Mv) of 15,000,000 or less, the entanglements of polymer chains can be suppressed to an appropriate range, and good molding processability can be obtained.

The viscosity-average molecular weight (Mv) is preferably 3,200,000 or more and 14,000,000 or less, more preferably 3,400,000 or more and 13,000,000 or less, further preferably 3,600,000 or more and 12,000,000 or less, and particularly preferably 3,800,000 to 10,000,000.

A method of measuring the viscosity-average molecular weight (Mv) will be described later.

In the present embodiment, as a method of regulating the viscosity-average molecular weight (Mv) within the above described range, for example, there is regulation of the polymerization temperature of a reactor upon the polymerization of the ethylene polymer. In general, as the polymerization temperature is set to be high, the molecular weight tends to be decreased, and as the polymerization temperature is set to be low, the molecular weight tends to be increased.

Moreover, as another method of regulating the viscosity-average molecular weight (Mv) within the above described range, there is addition of a chain-transfer agent such as hydrogen or alkylaluminum upon the polymerization of ethylene and the like. By adding such a chain-transfer agent to the reaction system, the molecular weight of the generated ethylene polymer tends to be decreased, even at the same constant polymerization temperature.

Furthermore, another method of regulating the viscosity-average molecular weight (Mv) within the above described range is optimization of a polymerization solvent. By enhancing the compatibility of the polymerization solvent with the obtained ethylene polymer, a high-molecular-weight ethylene polymer tends to be obtained. This is considered because a highly compatible solvent relatively easily enters into a consolidated polymer and is then dispersed therein, diffusion of monomers in the solvent is promoted, and thereby the concentration of dissolved monomers in the polymer is also increased. As a result, the polymerization degree of ethylene is increased, and a high-molecular-weight ethylene polymer can be obtained.

The polymerization solvent is not particularly limited. Examples of the polymerization solvent include: aliphatic hydrocarbons such as isobutane, pentane, isopentane, hexane, heptane, octane, decane, dodecane, and kerosene; alicyclic hydrocarbons such as cyclopentane, cyclohexane, and methylcyclopentane; aromatic hydrocarbons such as benzene, toluene, and xylene; halogenated hydrocarbons such as ethylene chloride, chlorobenzene, and dichloromethane; and mixtures thereof. As such a polymerization solvent, among others, an aliphatic hydrocarbon is preferable.

Further, as another method of regulating the viscosity-average molecular weight (Mv) within the above described range, it is also effective to use a polymerization catalyst, in which (B) a mesoporous structure compound is used as a catalyst carrier, as described later, and (B) the mesoporous structure compound is allowed to come into contact with (A) a transition metal compound, and thereafter, it is further allowed to come into contact with a substance having the function of modifying (A) the transition metal compound.

In the present embodiment, it is preferable to regulate the viscosity-average molecular weight (Mv) of the ethylene polymer by combining these methods.

[Quantity of Heat of Fusion Measured by Differential Scanning Calorimetry (DSC)]

In the ethylene polymer of the present embodiment, a first quantity of heat of fusion (hereinafter, the quantity of heat of fusion is also referred to as "the quantity of heat of fusion ΔH"), which is measured by differential scanning calorimetry (DSC) after giving heat history at 110° C. for 6 hours has been given to the ethylene polymer under a reduced pressure environment of 0.1 to 0.5 kPa, is 230 J/g or more and 293 J/g or less. The quantity of heat of fusion is preferably 230 J/g or more and 270 J/g or less, and more preferably 230 J/g or more and 260 J/g or less. Details of the measurement will be described later. The aforementioned quantity of heat of fusion is an estimated value measured by Perkin Elmer Pyris 1 DSC.

The ethylene polymer of the present embodiment is suitable for solid-phase stretch molding, as described later. Since the ethylene polymer is molded at a temperature that is the melting point or lower in the case of solid-phase stretch molding, the higher-order structure of the ethylene polymer dominates moldability. That is to say, in the solid-phase stretch molding, a low degree of entanglement of molecular chains becomes a great factor for dominating moldability.

The ethylene polymer having a low degree of entanglement of molecular chains has a small amorphous site, in which an entanglement structure is present, and a large crystal site, namely, it has a large quantity of heat of fusion. Thus, when the ethylene polymer of the present embodiment is used, stretching at a high ratio can be easily achieved, having a small entanglement structure. In addition, since the ethylene polymer of the present embodiment has a few defects, stretching unevenness is suppressed, the uniformity of mechanical strength is improved, and thereby, both good moldability and high strength can be achieved.

In the present embodiment, as a method of regulating the quantity of heat of fusion of the ethylene polymer within the above described range, for example, there is the use of a polymerization catalyst, in which (B) a mesoporous structure compound described later is used as a catalyst carrier, and the pore size of (B) the mesoporous structure compound is reduced. If such a compound obtained by reducing the pore size of (B) the mesoporous structure compound is used as a carrier of a polymerization catalyst, the quantity of heat of fusion of the ethylene polymer tends to be increased.

In addition, in the present embodiment, as a method of regulating the quantity of heat of fusion of the ethylene polymer within the above described range, for example, there is reduction in the amount of transition metal supported on a catalyst carrier. It is considered that, by reducing the amount of transition metal supported, active sites are sufficiently apart from one another, and substantial entanglement of polymers can be prevented during formation of the polymers.

Moreover, in the present embodiment, as another method of regulating the quantity of heat of fusion of the ethylene polymer within the above described range, it is also effective to use a polymerization catalyst, in which (B) a mesoporous structure compound is used as a catalyst carrier, as described later, and (B) the mesoporous structure compound is allowed to come into contact with (A) a transition metal compound, and thereafter, it is further allowed to come into contact with a substance having the function of modifying (A) the transition metal compound. By using such a carrier, the quantity of heat of fusion of the ethylene polymer becomes large. The reason therefore is unknown, but it is assumed that (A) the transition metal compound supported on the outer surface of a mesopore is preferentially inactivated by allowing it to come into contact with the substance having the function of modifying a catalyst species (transition metal compound), so that the polymerization reaction inside the mesopore can be preferentially advanced. It is assumed that, by performing polymerization under such conditions, molecular chains existing in mesopores, which are restricted to move and are easily crystallized, are relatively increased, and as a result, the quantity of heat of fusion of the ethylene polymer can be regulated within the above described range.

Conventionally, the molecular weight of an ethylene polymer has been conflicted to the degree of crystallinity thereof, and thus, it has been extremely difficult to achieve both of them. The present invention has discovered that conventionally non-executable means, namely, a step of inactivating a catalyst consisting of a mesoporous structure compound, particularly, on which (A) a transition metal compound is supported, is effectively carried out in order to achieve both a high molecular weight and a high degree of crystallinity (high quantity of heat of fusion).

It is to be noted that, as described later, (B) a mesoporous structure compound, in which reactive points other than those on the inner surfaces of mesopores have previously been inactivated, may also be used as a catalyst carrier.

Furthermore, in the present embodiment, in order to regulate the quantity of heat of fusion of the ethylene polymer within the above described range, optimization of a polymerization temperature or a stirring rate during polymerization, the use of an aliphatic hydrocarbon as a polymerization solvent, and application of ultrasonic wave to a catalyst are also effective, as described later.

[Plane Orientation Index Ratio]

In the ethylene polymer of the present embodiment, with regard to the ratio of the diffraction peak intensity of (200) plane to the diffraction peak intensity of (110) plane (hereinafter also referred to as a "200/110 plane orientation index"), which are obtained by X-ray diffractometry, the plane orientation index ratio (b)/(a), between 200/110 plane orientation index (a) in an unprocessed ethylene polymer and 200/110 plane orientation index (b) in a sheet which has been subjected to press processing and rolling processing under the below-mentioned conditions (1) to (3), is 7 or more. The plane orientation index ratio (b)/(a) is more preferably 10 or more, further preferably 13 or more, and particularly preferably 16 or more.

(1) 3 g of the ethylene polymer is pressed using a press molding machine at 130° C. at 11 MPa for 10 minutes.

(2) The resultant is cooled at 25° C. for 10 minutes, while maintaining the average pressure at 11 MPa.

(3) The obtained press sheet is heated at 140° C. for 3 minutes, and the resulting sheet is then compressed using a rolling mill having a temperature of 130° C. and a feeding rate of the roll of 1 m/min, to result in a stretch ratio of 6.

The 200/110 plane orientation index provides information regarding the plane orientation of (200) plane and (110) crystal plane to a roll plane in an ethylene polymer and a processed sheet. When the 200/110 plane orientation index is large, it is suggested that the (200) crystal plane is highly oriented parallel to the sheet plane. On the other hand, when crystals are randomly oriented, the peak area ratio between the (200) plane and the (110) plane has been known to be approximately 0.4.

When the plane orientation index ratio is within the aforementioned range, deformation is favorably done to external force applied during a step of rolling in the solid-phase stretching, the pressure bonding of polymers is also favorable, and uniform stretching load is easily applied, so that breaks or structural defects tend to be reduced. A detailed mechanism thereof has not been elucidated, but it is considered that since the present ethylene polymer has a few amorphous portions or hierarchical structures, the lamellar thickness and crystal size thereof are small, and it is a crystal structure that does not have crystals selectively growing in a uniaxial direction, the movement and deformation of the crystal portion of the ethylene polymer become easy, and thus, processability is improved.

The measurement method used in X-ray diffraction analysis will be described later.

In the present embodiment, as a method of regulating the above described plane orientation index ratio, regulation of the polymerization temperature of the ethylene polymer is applied. As the polymerization temperature is set at low, the plane orientation index ratio tends to be increased. The reason therefore is unknown. When the polymerization temperature is decreased, the polymerization rate is decreased and the crystallization rate is increased. Thus, the time of period at which molecular chains freely move becomes short, the thickening of lamella is suppressed, and the crystals become fine crystals. As a result, disorders occurring during stretch processing, such as deformation of fine crystals or displacement, are alleviated, and the crystals are considered to be easily highly oriented.

The polymerization temperature of the ethylene polymer is not particularly limited, and it is preferably −50° C. or higher and 100° C. or lower, more preferably −20° C. or higher and 60° C. or lower, further preferably 0° C. or higher and 50° C. or lower, and particularly preferably 10° C. or higher and 40° C. or lower.

In addition, in the present embodiment, as a method of regulating the above described orientation index ratio, it is also effective to regulate the stirring condition during polymerization, namely, rotation speed within a predetermined range. Specifically, the rotation speed is preferably 10 rpm to 300 rpm, more preferably 20 rpm to 200 rpm, further preferably 30 rpm to 100 rpm, and particularly preferably 30 rpm to 50 rpm. If the rotation speed is decreased, the above described plane orientation index ratio tends to be increased. In general, from the viewpoint of polymerization rate, yield and the like, the stirring speed has been generally set at high in the polymerization of ethylene. In the present embodiment, it has been discovered that the above described plane orientation index ratio can be regulated by carrying out a stirring operation at a low speed.

As another method of regulating the plane orientation index ratio, it is also effective to apply ultrasonic wave to a catalyst, before the catalyst is supplied to a polymerization apparatus.

Moreover, the impeller used for stirring is not particularly limited, and an inclined blade having an angle to the direction of a rotation shaft is preferable. This is because such an inclined blade can actively generate a radial flow in a polymerization reactor, so that it can disperse the generated polymer particle distribution to ensure the uniformity of particle density between the upper and lower sites of the reactor. It is assumed that the production method of decreasing the rotation speed within the above described range, the step of applying ultrasonic wave to the catalyst, and the form of the impeller are all established to favorably disperse the catalyst.

Furthermore, in the present embodiment, as another method of regulating the plane orientation index ratio of the ethylene polymer within the above described range, it is also effective to use a polymerization catalyst, in which (B) a mesoporous structure compound is used as a catalyst carrier, as described later, and (B) the mesoporous structure compound is allowed to come into contact with (A) a transition metal compound, and thereafter, it is further allowed to come into contact with a substance having the function of modifying (A) the transition metal compound. By using such a carrier, the plane orientation index ratio of the ethylene polymer can be increased. The reason therefore is unknown, but it is assumed that (A) the transition metal compound supported on the outer surface of a mesopore is preferentially inactivated by allowing it to come into contact with the substance having the function of modifying a catalyst species, so that the polymerization reaction inside the mesopore can be preferentially advanced. It is assumed that, by performing polymerization under such conditions, molecular chains existing in mesopores, which are restricted to move and are easily crystallized, are relatively increased, and as a result, the degree of orientation of molecular chains is improved, and the plane orientation index ratio of the ethylene polymer can be regulated within the above described range.

The present invention has discovered that conventionally non-executable means, namely, a step of inactivating a catalyst consisting of a mesoporous structure compound, particularly, on which (A) a transition metal compound is supported, is effectively carried out in order to achieve both a high molecular weight and a high degree of orientation (high plane orientation index ratio).

It is to be noted that, as described later, (B) a mesoporous structure compound, in which reactive points other than those on the inner surfaces of mesopores have previously been inactivated, may also be used as a carrier of a polymerization catalyst.

[Melting Point in Differential Scanning Calorimetry]

In the ethylene polymer of the present embodiment, with regard to a first melting point ($Tm_1$) measured by differential scanning calorimetry (DSC), when the melting point ($Tm_{1a}$) of the unprocessed ethylene polymer and the melting point ($Tm_{1b}$) of sheet subjected to press processing and rolling processing under the below-mentioned conditions (1) to (3) are measured, the difference in the melting point ($Tm_{1b}-Tm_{1a}$) is preferably 3.0° C. or more. The difference in the melting point ($Tm_{1b}-Tm_{1a}$) is preferably 3.3° C. or more, and more preferably 3.5° C. or more. As a method of measuring the melting point, an estimated value measured by Perkin Elmer Pyris 1 DSC is used, as in the case of the above described quantity of heat of fusion.

(1) 3 g of the ethylene polymer is pressed using a press molding machine at 130° C. at 11 MPa for 10 minutes.

(2) The resultant is cooled at 25° C. for 10 minutes, while maintaining the average pressure at 11 MPa.

(3) The obtained press sheet is heated at 140° C. for 3 minutes, and the resulting sheet is then compressed using a rolling mill having a temperature of 130° C. and a feeding rate of the roll of 1 m/min, to result in a stretch ratio of 6.

By setting the difference in the melting point ($Tm_{1b}-Tm_{1a}$) to be 3.0° C. or more, the mechanical strength of a stretch-molded product can be increased, and the uniformity also tends to be improved. The reason therefore is unknown, but it is assumed that an increase in the melting point leads to the easy achievement of the thickening of a lamella length during the stretch processing, and thus that a lamellar structure in which molecular chains are regularly aligned can be newly constructed in an orientation state in which deformation of molecular chains in a folded lamellar crystal easily takes place.

In the present embodiment, as a method of regulating the difference in the melting point ($Tm_{1b}-Tm_{1a}$) within the above described range, for example, there is the use of a polymerization catalyst, in which (B) a mesoporous structure compound described later is used as a catalyst carrier, and the pore size of the mesoporous structure compound is reduced. By reducing the pore size, the difference in the melting point tends to be increased.

Moreover, as other methods of regulating the difference in the melting point ($Tm_{1b}-Tm_{1a}$) within the above described range, optimization of a polymerization temperature or a stirring rate during polymerization, the use of an aliphatic hydrocarbon as a polymerization solvent, and application of ultrasonic wave to a catalyst are also effective, as described later.

The ethylene polymer of the present embodiment may comprise additives such as a neutralizer, an antioxidant and a light stabilizer.

The neutralizer is used as a halogen catcher for catching halogen such as chlorine comprised in the ethylene polymer, a molding processing aid, or the like.

The neutralizer is not particularly limited, and examples of the neutralizer include stearates of alkaline earth metals such as calcium, magnesium and barium. The content of the neutralizer is not particularly limited, and it is, for example, 5000 ppm or less, preferably 4000 ppm or less, and more preferably 3000 ppm or less.

The antioxidant is not particularly limited, and examples of the antioxidant include phenolic antioxidants such as dibutylhydroxytoluene, pentaerithrityl-tetrakis[3-(3,5-di-t-butyl-4-hydroxyphenyl)propionate], and octadecyl-3-(3,5-di-t-butyl-4-hydroxyphenyl)propionate. The content of the antioxidant is not particularly limited, and it is, for example, 5000 ppm or less, preferably 4000 ppm or less, and more preferably 3000 ppm or less.

The light stabilizer is not particularly limited, and examples of the light stabilizer include: benzotriazole-based light stabilizers such as 2-(5-methyl-2-hydroxyphenyl)benzotriazole and 2-(3-t-butyl-5-methyl-2-hydroxyphenyl)-5-chlorobenzotriazole; and hindered amine-based light stabilizers such as bis(2,2,6,6-tetramethyl-4-piperidine)sebacate and poly[{6-(1,1,3,3-tetramethylbutyl)amino-1,3,5-triazine-2,4-diyl}{(2,2,6,6-tetramethyl-4-piperidyl)imino}hexamethylene{(2,2,6,6-tetramethyl-4-piperidyl)imino}]. The content of the light stabilizer is not particularly limited, and it is, for example, 5000 ppm or less, preferably 4000 ppm or less, and more preferably 3000 ppm or less.

The content of additives comprised in the ethylene polymer can be obtained by extracting the additives in the ethylene polymer using tetrahydrofuran (THF) according to Soxhlet extraction for 6 hours, and then separating and quantifying the extract by liquid chromatography.

[Method for Producing Ethylene Polymer]

As described above, in the method for producing the ethylene polymer of the present embodiment, a catalyst can be used during polymerization. As a catalyst, a known polymerization catalyst used in the polymerization of olefin can be used. Examples of such a catalyst include a catalyst prepared by supporting an after-mentioned transition metal compound on a carrier, and a combination of the aforementioned catalyst with a co-catalyst.

First, a polymerization catalyst used for the production of the ethylene polymer will be described.

[(A) Transition Metal Compound]

As a transition metal compound, a transition metal compound, which has been conventionally used in the polymerization of olefin, can be used without limitation. Among others, transition metal compounds (I-1) to (I-4) of group 4 of the periodic table, comprising a ligand having a cyclopentadienyl skeleton, or a transition metal compound (II) having an annular η-binding anionic ligand, as shown below, are preferable. In particular, the compound (I-2) is particularly preferably used.

(A) The transition metal compound of group 4 of the periodic table, comprising a ligand having a cyclopentadienyl skeleton is, for example, a transition metal compound represented by the following general formula (I-1).

$$M^1L_x \quad (I\text{-}1)$$

In the above formula, $M^1$ represents a transition metal atom selected from group 4 of the periodic table, and it is specifically zirconium, titanium or hafnium, and is preferably zirconium. In addition, x represents a number satisfying the valence of the transition metal atom $M^1$, and it represents the number of ligands L that are coordinated to the transition metal atom $M^1$. L represents a ligand coordinated to the transition metal atom, and at least one L is a ligand having a cyclopentadienyl skeleton. L other than the ligand having a cyclopentadienyl skeleton is a hydrocarbon group containing 1 to 20 carbon atoms, a halogenated hydrocarbon group containing 1 to 20 carbon atoms, an oxygen-containing group, a sulfur-containing group, a silicon-containing group, a halogen atom, or a hydrogen atom.

Examples of the ligand having a cyclopentadienyl skeleton include a cyclopentadienyl group, alkyl-substituted cyclopentadienyl groups such as a methylcyclopentadienyl group, a dimethylcyclopentadienyl group, a trimethylcyclopentadienyl group, a tetramethylcyclopentadienyl group, a pentamethylcyclopentadienyl group, an ethylcyclopentadienyl group, a methylethylcyclopentadienyl group, a propylcyclopentadienyl group, a methylpropylcyclopentadienyl group, a butylcyclopentadienyl group, a methylbutylcyclopentadienyl group and a hexylcyclopentadienyl group, an indenyl group, a 4,5,6,7-tetrahydroindenyl group, and a fluorenyl group. These groups may be optionally substituted with a (halogenated) hydrocarbon group containing 1 to 20 carbon atoms, an oxygen-containing group, a sulfur-containing group, a silicon-containing group, a halogen atom, and the like.

When the compound represented by the above general formula (I-1) comprises two or more ligands having a cyclopentadienyl skeleton, among the ligands, two ligands having a cyclopentadienyl skeleton may be bound to each other via a divalent linking group such as a (substituted) alkylene group or a (substituted) silylene group. An example of the transition metal compound, in which such two ligands having a cyclopentadienyl skeleton are bound to each other via a divalent linking group, is a transition metal compound represented by the general formula (I-3), as shown later.

Specific examples of the ligand L other than the ligand having a cyclopentadienyl skeleton are given below.

Examples of the hydrocarbon group containing 1 to 20 carbon atoms include an alkyl group, a cycloalkyl group, an alkenyl group, an arylalkyl group and an aryl group, and more specific examples include: alkyl groups such as methyl, ethyl, propyl, butyl, hexyl, octyl, nonyl, dodecyl, and eicosyl; cycloalkyl groups such as cyclopentyl, cyclohexyl, norbornyl, and adamantyl; alkenyl groups such as vinyl, propenyl, and cyclohexenyl; arylalkyl groups such as benzyl, phenylethyl, and phenylpropyl; and aryl groups such as phenyl, tolyl, dimethylphenyl, trimethylphenyl, ethylphenyl, propylphenyl, biphenylyl, naphthyl, methylnaphthyl, anthryl, and phenanthryl.

An example of the halogenated hydrocarbon group containing 1 to 20 carbon atoms is the above described hydrocarbon group containing 1 to 20 carbon atoms, which is substituted with halogen.

Specific examples of the oxygen-containing group include: hydroxy groups; alkoxy groups such as methoxy, ethoxy, propoxy, and butoxy; aryloxy groups such as phenoxy, methylphenoxy, dimethylphenoxy, and naphthoxy; and arylalkoxy groups such as phenylmethoxy and phenylethoxy.

Specific examples of the sulfur-containing group include: substituents obtained by substituting oxygen in the above described oxygen-containing groups with sulfur, and sulfonate groups such as methyl sulfonate, trifluoromethane sulfonate, phenyl sulfonate, benzyl sulfonate, p-toluene sulfonate, trimethylbenzene sulfonate, triisobutylbenzene sulfonate, p-chlorobenzene sulfonate, and pentafluorobenzene sulfonate; and sulfinate groups such as methyl sulfinate, phenyl sulfinate, benzyl sulfinate, p-toluene sulfinate, trimethylbenzene sulfinate, and pentafluorobenzene sulfinate.

Specific examples of the silicon-containing group include: monohydrocarbon-substituted silyl such as methylsilyl and phenylsilyl; dihydrocarbon-substituted silyl such as dimethylsilyl and diphenylsilyl; trihydrocarbon-substituted silyl such as trimethylsilyl, triethylsilyl, tripropylsilyl, tricyclohexylsilyl, triphenylsilyl, dimethylphenylsilyl, methyldiphenylsilyl, tritolylsilyl, and trinaphthylsilyl; silyl ether of hydrocarbon-substituted silyl, such as trimethylsilyl ether; silicon-substituted alkyl groups such as trimethylsilylmethyl; and silicon-substituted aryl groups such as trimethylsilylphenyl.

Examples of the halogen atom include a fluorine atom, a chlorine atom, a bromine atom, and an iodine atom.

When the valence of transition metal is 4, for example, such a transition metal compound is more specifically represented by the following general formula (I-2).

$$R^1R^2R^3R^4M^1 \quad (I\text{-}2)$$

In the above formula, $M^1$ represents a transition metal atom selected from the same group 4 of the periodic table as described above, and it is preferably a zirconium atom.

$R^1$ represents a group having a cyclopentadienyl skeleton (a ligand), and $R^2$, $R^3$ and $R^4$, which may be the same or different, each represent a group having a cyclopentadienyl skeleton (a ligand), a (halogenated) hydrocarbon group containing 1 to 20 carbon atoms, an oxygen-containing group, a sulfur-containing group, a silicon-containing group, a halogen atom, or a hydrogen atom.

In the present embodiment, a compound wherein, in the transition metal compound represented by the above general formula (I-2), at least one of $R^2$, $R^3$ and $R^4$ is a group having a cyclopentadienyl skeleton (a ligand), for example, a compound wherein $R^1$ and $R^2$ represent a group having a cyclopentadienyl skeleton (a ligand), is preferably used. In addition, when each of $R^1$ and $R^2$ is a group having a cyclopentadienyl skeleton (a ligand), each of $R^3$ and $R^4$ is preferably a group having a cyclopentadienyl skeleton, an alkyl group, a cycloalkyl group, an alkenyl group, an arylalkyl group, an aryl group, an alkoxy group, an aryloxy group, a trialkylsilyl group, a sulfonate group, a halogen atom, or a hydrogen atom.

Specific examples of the transition metal compound represented by the above general formula (I-1), wherein $M^1$ is zirconium, will be given below:

bis(indenyl)zirconium dichloride,
bis(indenyl)zirconium dibromide,
bis(indenyl)zirconium bis(p-toluene sulfonate),
bis(4,5,6,7-tetrahydroindenyl)zirconium dichloride,
bis(fluorenyl)zirconium dichloride,
bis(cyclopentadienyl)zirconium dichloride,
bis(cyclopentadienyl)zirconium dibromide,
bis(cyclopentadienyl)methylzirconium monochloride,
bis(cyclopentadienyl)ethylzirconium monochloride,
bis(cyclopentadienyl)cyclohexylzirconium monochloride,
bis(cyclopentadienyl)phenylzirconium monochloride,
bis(cyclopentadienyl)benzylzirconium monochloride,
bis(cyclopentadienyl)zirconium monochloride monohydride,
bis(cyclopentadienyl)methylzirconium monohydride,
bis(cyclopentadienyl)dimethylzirconium,
bis(cyclopentadienyl)diphenylzirconium,
bis(cyclopentadienyl)dibenzylzirconium,
bis(cyclopentadienyl)zirconium methoxychloride
bis(cyclopentadienyl)zirconium ethoxychloride,
bis(cyclopentadienyl)zirconium bis(methane sulfonate),
bis(cyclopentadienyl)zirconium bis(p-toluene sulfonate),
bis(cyclopentadienyl)zirconium bis(trifluoromethane sulfonate),
bis(methylcyclopentadienyl)zirconium dichloride,
bis(dimethylcyclopentadienyl)zirconium dichloride,
bis(dimethylcyclopentadienyl)zirconium ethoxychloride,
bis(dimethylcyclopentadienyl)zirconium bis(trifluoromethane sulfonate),
bis(ethylcyclopentadienyl)zirconium dichloride,
bis(methylethylcyclopentadienyl)zirconium dichloride,
bis(propylcyclopentadienyl)zirconium dichloride,
bis(methylpropylcyclopentadienyl)zirconium dichloride,
bis(butylcyclopentadienyl)zirconium dichloride,
bis(methylbutylcyclopentadienyl)zirconium dichloride,
bis(methylbutylcyclopentadienyl)zirconium bis(methane sulfonate),
bis(trimethylcyclopentadienyl)zirconium dichloride,
bis(tetramethylcyclopentadienyl)zirconium dichloride,
bis(pentamethylcyclopentadienyl)zirconium dichloride,
bis(hexylcyclopentadienyl)zirconium dichloride, and
bis(trimethylsilylcyclopentadienyl)zirconium dichloride.

It is to be noted that, in the aforementioned examples, the disubstituted form of a cyclopentadienyl ring includes 1,2- and 1,3-substituted forms, and the trisubstituted form of a cyclopentadienyl ring includes 1,2,3- and 1,2,4-substituted forms. In addition, alkyl groups, such as propyl or butyl, include n-, i-, sec-, tert-isomers.

Moreover, examples of the transition metal compound also include the aforementioned zirconium compounds, zirconium of which is substituted with titanium or hafnium. An example of the transition metal compound, in which two ligands having a cyclopentadienyl skeleton are bound to each other via a divalent linking group, is a compound represented by the following formula (I-3):

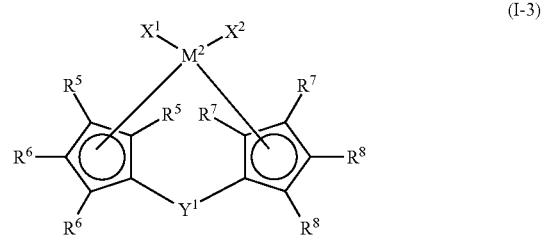

In the above formula, $M^2$ represents a transition metal atom of group 4 of the periodic table, and it is specifically zirconium, titanium or hafnium, and is preferably zirconium. $R^5$, $R^6$, $R^7$ and $R^8$, which may be the same or different, each represent a hydrocarbon group containing 1 to 20 carbon atoms, a halogenated hydrocarbon group containing 1 to 20 carbon atoms, an oxygen-containing group, a sulfur-containing group, a silicon-containing group, a nitrogen-containing group, a phosphorus-containing group, a halogen atom, or a hydrogen atom. Among the groups represented by $R^5$, $R^6$, $R^7$ and $R^8$, some of the groups adjacent to each other may be bound to each other, and may form a ring, together with carbon atoms to which those groups bind. It is to be noted that $R^5$, $R^6$, $R^7$ and $R^8$ are each displayed at two sites, and that, for example, $R^5$ and $R^5$ may be groups, which are the same as or different from each other. The groups represented by R, which have the same symbols, indicate a preferred combination of groups, which are to be bound to each other to form a ring.

Examples of the hydrocarbon group containing 1 to 20 carbon atoms include the same groups as those exemplified for the above described L, such as an alkyl group, a cycloalkyl group, an alkenyl group, an arylalkyl group, and an aryl group.

Examples of a ring formed by the binding of these hydrocarbon groups include condensed ring groups such as a benzene ring, a naphthalene ring, an acenaphthene ring and an indene ring, and the above described condensed ring groups, the hydrogen atom on which is substituted with an alkyl group such as methyl, ethyl, propyl or butyl.

An example of the halogenated hydrocarbon group containing 1 to 20 carbon atoms is the above described hydrocarbon group containing 1 to 20 carbon atoms, which is substituted with halogen.

Examples of the oxygen-containing group include a hydroxy group, and the same alkoxy group, aryloxy group and arylalkoxy group as those exemplified for the above described L.

An example of the sulfur-containing group is a substituent obtained by substituting oxygen in the above described oxygen-containing group with sulfur.

Examples of the silicon-containing group include silyl ethers of monohydrocarbon-substituted silyl, dihydrocarbon-substituted silyl, trihydrocarbon-substituted silyl and hydrocarbon-substituted silyl, which are the same as those exemplified for the above described L, a silicon-substituted alkyl group, and a silicon-substituted aryl group.

Examples of the nitrogen-containing group include: amino groups; alkylamino groups such as methylamino, dimethylamino, diethylamino, dipropylamino, dibutylamino, and dicyclohexylamino; and arylamino groups or alkylarylamino groups, such as phenylamino, diphenylamino, ditolylamino, dinaphthylamino, and methylphenylamino.

Examples of the phosphorus-containing group include phosphino groups such as dimethylphosphino and diphenylphosphino.

Examples of the halogen atom include the same as those exemplified for the above described L.

Among these groups, a hydrocarbon group containing 1 to 20 carbon atoms or a hydrogen atom is preferable, and further, a hydrocarbon group containing 1 to 4 carbon atoms, such as methyl, ethyl, propyl or butyl, a benzene ring formed by the binding of hydrocarbon groups, and a benzene ring formed by the binding of hydrocarbon groups, the hydrogen atom on which is substituted with an alkyl group such as methyl, ethyl, n-propyl, iso-propyl, n-butyl, iso-butyl or tert-butyl, are particularly preferable.

In the above formula, $X^1$ and $X^2$, which may be the same or different, each represent a hydrocarbon group containing 1 to 20 carbon atoms, a halogenated hydrocarbon group containing 1 to 20 carbon atoms, an oxygen-containing group, a sulfur-containing group, a silicon-containing group, a hydrogen atom, or a halogen atom.

Examples of the hydrocarbon group containing 1 to 20 carbon atoms include the same groups as those exemplified for the above described L, such as an alkyl group, a cycloalkyl group, an alkenyl group, an arylalkyl group, and an aryl group.

An example of the halogenated hydrocarbon group containing 1 to 20 carbon atoms is the above described hydrocarbon group containing 1 to 20 carbon atoms, which is substituted with halogen. Examples of the oxygen-containing group include a hydroxy group, and an alkoxy group, an aryloxy group and an arylalkoxy group, which are the same as those exemplified for the above described L.

Examples of the sulfur-containing group include a substituent obtained by substituting oxygen in the above described oxygen-containing group with sulfur, and a sulfonate group and a sulfinate group, which are the same as those exemplified for the above described L. Examples of the silicon-containing group include a silicon-substituted alkyl group and a silicon-substituted aryl group, which are the same as those for the above described L.

Examples of the halogen atom include the same groups and atoms as those exemplified for the above described L. Among these groups and atoms, a halogen atom, a hydrocarbon group containing 1 to 20 carbon atoms, or a sulfonate group is preferable.

In the above formula, $Y^1$ represents a divalent hydrocarbon group containing 1 to 20 carbon atoms, a divalent halogenated hydrocarbon group containing 1 to 20 carbon atoms, a divalent silicon-containing group, a divalent germanium-containing group, a divalent tin-containing group, —O—, —CO—, —S—, —SO—, —SO$_2$—, —Ge—, —Sn—, —NR$^9$—, —P(R$^9$)—, —P(O)(R$^9$)—, —BR$^9$—, or AlR$^9$— (wherein R$^9$, which may be the same or different, each represent a hydrocarbon group containing 1 to 20 carbon atoms, a halogenated hydrocarbon group containing 1 to 20 carbon atoms, a hydrogen atom, or a halogen atom).

Specific examples of the divalent hydrocarbon group containing 1 to 20 carbon atoms include: alkylene groups such as methylene, dimethylmethylene, 1,2-ethylene, dimethyl-1,2-ethylene, 1,3-trimethylene, 1,4-tetramethylene, 1,2-cyclohexylene, and 1,4-cyclohexylene; and arylalkylene groups such as diphenylmethylene and diphenyl-1,2-ethylene.

Specific examples of the divalent halogenated hydrocarbon group containing 1 to 20 carbon atoms include groups obtained by halogenating the above described divalent hydrocarbon groups containing 1 to 20 carbon atoms, such as chloromethylene.

Examples of the divalent silicon-containing group include: alkylsilylene groups such as silylene, methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene, and di(p-chlorophenyl)silylene; alkylarylsilylene groups; arylsilylene groups; alkyldisilylene groups such as tetramethyl-1,2-disilylene and tetraphenyl-1,2-disilylene; alkylaryldisilylene groups; and aryldisilylene groups.

An example of the divalent germanium-containing group is the above described divalent silicon-containing group, silicon of which is substituted with germanium.

An example of the divalent tin-containing group is the above described divalent silicon-containing group, silicon of which is substituted with tin.

In addition, R$^9$ represents a hydrocarbon group containing 1 to 20 carbon atoms, a halogenated hydrocarbon group containing 1 to 20 carbon atoms, or a halogen atom, which are the same as those exemplified for the above described L. Among these groups, a substituted silylene group such as dimethylsilylene, diphenylsilylene or methylphenylsilylene is particularly preferable.

Specific examples of the transition metal compound represented by the above general formula (I-3) will be given below:

ethylene-bis(indenyl)dimethylzirconium,
ethylene-bis(indenyl)zirconium dichloride,
ethylene-bis(indenyl)zirconium bis(trifluoromethane sulfonate),
ethylene-bis(indenyl)zirconium bis(methane sulfonate),
ethylene-bis(indenyl)zirconium bis(p-toluene sulfonate),
ethylene-bis(indenyl)zirconium bis(p-chlorobenzene sulfonate),
ethylene-bis(4,5,6,7-tetrahydroindenyl)zirconium dichloride,
isopropylidene-bis(cyclopentadienyl) (fluorenyl)zirconium dichloride,
isopropylidene-bis(cyclopentadienyl) (methylcyclopentadienyl)zirconium dichloride, dimethylsilylene-bis(cyclopentadienyl)zirconium dichloride,
dimethylsilylene-bis(methylcyclopentadienyl)zirconium dichloride,
dimethylsilylene-bis(dimethylcyclopentadienyl)zirconium dichloride,
dimethylsilylene-bis(trimethylcyclopentadienyl)zirconium dichloride,
dimethylsilylene-bis(indenyl)zirconium dichloride,
dimethylsilylene-bis(indenyl)zirconium bis(trifluoromethane sulfonate),
dimethylsilylene-bis(4,5,6,7-tetrahydroindenyl)zirconium dichloride,
dimethylsilylene-bis(cyclopentadienyl) (fluorenyl)zirconium dichloride,
diphenylsilylene-bis(indenyl)zirconium dichloride,
methylphenylsilylene-bis(indenyl)zirconium dichloride,
rac-dimethylsilylene-bis(2,3,5-trimethylcyclopentadienyl) zirconium dichloride,
rac-dimethylsilylene-bis(2,4,7-trimethylcyclopentadienyl) zirconium dichloride,
rac-dimethylsilylene-bis(2-methyl-4-tert-butylcyclopentadienyl)zirconium dichloride,
isopropylidene-(cyclopentadienyl) (fluorenyl)zirconium dichloride,
dimethylsilylene-(3-tert-butylcyclopentadienyl) (indenyl) zirconium dichloride,
isopropylidene-(4-methylcyclopentadienyl) (3-methylindenyl)zirconium dichloride,
isopropylidene-(4-tert-butylcyclopentadienyl) (3-methylindenyl)zirconium dichloride,
isopropylidene-(4-tert-butylcyclopentadienyl) (3-tert-butylindenyl) zirconium dichloride,
dimethylsilylene-(4-methylcyclopentadienyl) (3-methylindenyl)zirconium dichloride,
dimethylsilylene-(4-tert-butylcyclopentadienyl) (3-methylindenyl)zirconium dichloride,
dimethylsilylene-(4-tert-butylcyclopentadienyl) (3-tert-butylindenyl)zirconium dichloride,
dimethylsilylene-(3-tert-butylcyclopentadienyl) (fluorenyl) zirconium dichloride, and
isopropylidene-(3-tert-butylcyclopentadienyl) (fluorenyl) zirconium dichloride.

Moreover, another example of the transition metal compound represented by the above formula (I-3) is the aforementioned compounds, zirconium of which is substituted with titanium or hafnium. A more specific example of the transition metal compound represented by the above formula (I-3) is a transition metal compound represented by the following formula (I-4):

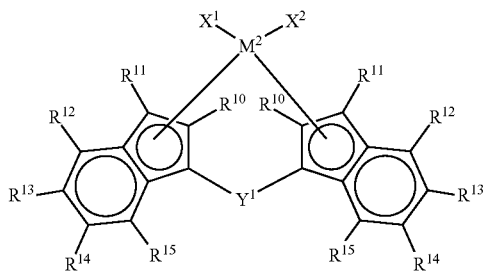

(I-4)

In the above formula, $M^2$ represents a transition metal atom of group 4 of the periodic table, and it is specifically titanium, zirconium or hafnium, and is preferably zirconium. $R^{10}$, which may be the same or different, each represent a hydrocarbon group containing 1 to 6 carbon atoms, and specific examples include: alkyl groups such as methyl, ethyl, n-propyl, isopropyl, n-butyl, isobutyl, sec-butyl, tert-butyl, n-pentyl, neopentyl, n-hexyl, and cyclohexyl; and alkenyl groups such as vinyl and propenyl.

Among these groups, an alkyl group whose carbon atom binding to an indenyl group is primary is preferable, an alkyl group containing 1 to 4 carbon atoms is more preferable, and a methyl group and an ethyl group are particularly preferable.

In the above formula, $R^{11}$, $R^{13}$, $R^{14}$ and $R^{15}$, which may be the same or different, each represent a hydrogen atom, a halogen atom, or the same hydrocarbon groups containing 1 to 6 carbon atoms as those of $R^{10}$. $R^{12}$, which may be the same or different, each represent a hydrogen atom or an aryl group containing 6 to 16 carbon atoms, and specific examples include phenyl, α-naphthyl, β-naphthyl, anthryl, phenanthryl, pyrenyl, acenaphthyl, phenalenyl, aceanthrylenyl, tetrahydronaphthyl, indanyl, and biphenylyl. Among these groups, phenyl, naphthyl, anthryl, and phenanthryl are preferable.

These aryl groups may be optionally substituted with: halogen atoms such as fluorine, chlorine, bromine, and iodine; alkyl groups such as methyl, ethyl, propyl, butyl, hexyl, cyclohexyl, octyl, nonyl, dodecyl, eicosyl, norbornyl, and adamantyl; alkenyl groups such as vinyl, propenyl, and cyclohexenyl; arylalkyl groups such as benzyl, phenylethyl, and phenylpropyl; hydrocarbon groups containing 1 to 20 carbon atoms, including aryl groups such as phenyl, tolyl, dimethylphenyl, trimethylphenyl, ethylphenyl, propylphenyl, biphenyl, α- or β-naphthyl, methylnaphthyl, anthryl, phenanthryl, benzylphenyl, pyrenyl, acenaphthyl, phenalenyl, aceanthrylenyl, tetrahydronaphthyl, indanyl, and biphenylyl; and organic silyl groups such as trimethylsilyl, triethylsilyl, and triphenylsilyl.

In the above formula, $X^1$ and $X^2$, which may be the same or different, each represent the same groups as those exemplified for $X^1$ and $X^2$ in the above general formula (I-3). Among these groups, a halogen atom, or a hydrocarbon group containing 1 to 20 carbon atoms is preferable.

In the above formula, $Y^1$ represents the same groups as those exemplified for $Y^1$ in the above general formula (I-3). Among these groups, a divalent silicon-containing group and a divalent germanium-containing group are preferable, a divalent silicon-containing group is more preferable, and alkylsilylene, alkylarylsilylene or arylsilylene is further preferable.

Specific examples of the transition metal compound represented by the above general formula (I-4) will be given below:
rac-dimethylsilylene-bis{1-(2-methyl-4-phenylindenyl)} zirconium dichloride,
rac-dimethylsilylene-bis{1-(2-methyl-4-(α-naphthyl)indenyl)}zirconium dichloride,
rac-dimethylsilylene-bis{1-(2-methyl-4-(β-naphthyl)indenyl)}zirconium dichloride,
rac-dimethylsilylene-bis{1-(2-methyl-4-(1-anthryl)indenyl)} zirconium dichloride,
rac-dimethylsilylene-bis{1-(2-methyl-4-(2-anthryl)indenyl)} zirconium dichloride,
rac-dimethylsilylene-bis{1-(2-methyl-4-(9-anthryl)indenyl)} zirconium dichloride,
rac-dimethylsilylene-bis{1-(2-methyl-4-(9-phenanthryl)indenyl)}zirconium dichloride, rac-dimethylsilylene-bis{1-(2-methyl-4-(p-fluorophenyl)indenyl)}zirconium dichloride,
rac-dimethylsilylene-bis{1-(2-methyl-4-(pentafluorophenyl)indenyl)}zirconium dichloride,
rac-dimethylsilylene-bis{1-(2-methyl-4-(p-chlorophenyl)indenyl)}zirconium dichloride,
rac-dimethylsilylene-bis{1-(2-methyl-4-(m-chlorophenyl)indenyl)}zirconium dichloride,
rac-dimethylsilylene-bis{1-(2-methyl-4-(o-chlorophenyl)indenyl)}zirconium dichloride,
rac-dimethylsilylene-bis{1-(2-methyl-4-(o,p-dichlorophenyl)phenylindenyl)}zirconium dichloride,
rac-dimethylsilylene-bis{1-(2-methyl-4-(p-bromophenyl)indenyl)}zirconium dichloride,
rac-dimethylsilylene-bis{1-(2-methyl-4-(p-tolyl)indenyl)}zirconium dichloride,
rac-dimethylsilylene-bis{1-(2-methyl-4-(m-tolyl)indenyl)}zirconium dichloride,
rac-dimethylsilylene-bis{1-(2-methyl-4-(o-tolyl)indenyl)}zirconium dichloride,
rac-dimethylsilylene-bis{1-(2-methyl-4-(o,o'-dimethylphenyl)-1-indenyl)zirconium dichloride,
rac-dimethylsilylene-bis{1-(2-methyl-4-(p-ethylphenyl)indenyl)}zirconium dichloride,
rac-dimethylsilylene-bis{1-(2-methyl-4-(pi-propylphenyl)indenyl)}zirconium dichloride,
rac-dimethylsilylene-bis{1-(2-methyl-4-(p-benzylphenyl)indenyl)}zirconium dichloride,
rac-dimethylsilylene-bis{1-(2-methyl-4-(p-biphenyl)indenyl)}zirconium dichloride,
rac-dimethylsilylene-bis{1-(2-methyl-4-(m-biphenyl)indenyl)}zirconium dichloride,
rac-dimethylsilylene-bis{1-(2-methyl-4-(p-trimethylsilylenephenyl)indenyl)}zirconium dichloride,
rac-dimethylsilylene-bis{1-(2-methyl-4-(m-trimethylsilylenephenyl)indenyl)}zirconium dichloride,
rac-dimethylsilylene-bis{1-(2-phenyl-4-phenylindenyl)}zirconium dichloride,
rac-diethylsilylene-bis{1-(2-methyl-4-phenylindenyl)}zirconium dichloride,
rac-di-(i-propyl) silylene-bis{1-(2-methyl-4-phenylindenyl)} zirconium dichloride,
rac-di-(n-butyl) silylene-bis{1-(2-methyl-4-phenylindenyl)}zirconium dichloride,
rac-dicyclohexylsilylene-bis{1-(2-methyl-4-phenylindenyl)}zirconium dichloride,
rac-methylphenylsilylene-bis{1-(2-methyl-4-phenylindenyl)}zirconium dichloride,
rac-diphenylsilylene-bis{1-(2-methyl-4-phenylindenyl)}zirconium dichloride,
rac-di(p-tolyl) silylene-bis{1-(2-methyl-4-phenylindenyl)}zirconium dichloride,
rac-di(p-chlorophenyl) silylene-bis{1-(2-methyl-4-phenylindenyl)}zirconium dichloride,
rac-methylene-bis{1-(2-methyl-4-phenylindenyl)}zirconium dichloride,
rac-ethylene-bis{1-(2-methyl-4-phenylindenyl)}zirconium dichloride,
rac-dimethylgermylene-bis{1-(2-methyl-4-phenylindenyl)}zirconium dichloride,
rac-dimethylstannylene-bis{1-(2-methyl-4-phenylindenyl)}zirconium dichloride,
rac-dimethylsilylene-bis{1-(2-methyl-4-phenylindenyl)}zirconium dibromide,
rac-dimethylsilylene-bis{1-(2-methyl-4-phenylindenyl)}zirconiumdimethyl,
rac-dimethylsilylene-bis{1-(2-methyl-4-phenylindenyl)}zirconiummethyl chloride,
rac-dimethylsilylene-bis{1-(2-methyl-4-phenylindenyl)}zirconium dichloride SO$_2$Me,
rac-dimethylsilylene-bis{1-(2-methyl-4-phenylindenyl)}zirconium dichloride OSO$_2$Me,
rac-dimethylsilylene-bis{1-(2-ethyl-4-phenylindenyl)}zirconium dichloride,
rac-dimethylsilylene-bis{1-(2-ethyl-4-(α-naphthyl)indenyl)} zirconium dichloride,
rac-dimethylsilylene-bis{1-(2-ethyl-4-(β-naphthyl)indenyl)} zirconium dichloride,
rac-dimethylsilylene-bis{1-(2-ethyl-4-(2-methyl-1-naphthyl)indenyl)}zirconium dichloride,
rac-dimethylsilylene-bis{1-(2-ethyl-4-(5-acenaphthyl)indenyl)}zirconium dichloride,
rac-dimethylsilylene-bis{1-(2-ethyl-4-(9-anthryl)indenyl)} zirconium dichloride,
rac-dimethylsilylene-bis{1-(2-ethyl-4-(9-phenanthryl)indenyl)}zirconium dichloride,
rac-dimethylsilylene-bis{1-(2-ethyl-4-(o-methylphenyl)indenyl)}zirconium dichloride,
rac-dimethylsilylene-bis{1-(2-ethyl-4-(m-methylphenyl)indenyl)}zirconium dichloride,
rac-dimethylsilylene-bis{1-(2-ethyl-4-(p-methylphenyl)indenyl)}zirconium dichloride,
rac-dimethylsilylene-bis{1-(2-ethyl-4-(2,3-dimethylphenyl)indenyl)}zirconium dichloride,
rac-dimethylsilylene-bis{1-(2-ethyl-4-(2,4-dimethylphenyl)indenyl)}zirconium dichloride,
rac-dimethylsilylene-bis{1-(2-ethyl-4-(2,5-dimethylphenyl)indenyl)}zirconium dichloride,
rac-dimethylsilylene-bis{1-(2-ethyl-4-(2,4,6-trimethylphenyl)indenyl)}zirconium dichloride,
rac-dimethylsilylene-bis{1-(2-ethyl-4-(o-chlorophenyl)indenyl)}zirconium dichloride,
rac-dimethylsilylene-bis{1-(2-ethyl-4-(m-chlorophenyl)indenyl)}zirconium dichloride,
rac-dimethylsilylene-bis{1-(2-ethyl-4-(p-chlorophenyl)indenyl)}zirconium dichloride,
rac-dimethylsilylene-bis{1-(2-ethyl-4-(2,3-dichlorophenyl)indenyl)}zirconium dichloride,
rac-dimethylsilylene-bis{1-(2-ethyl-4-(2,6-dichlorophenyl)indenyl)}zirconium dichloride,
rac-dimethylsilylene-bis{1-(2-ethyl-4-(3,5-dichlorophenyl)indenyl)}zirconium dichloride,
rac-dimethylsilylene-bis{1-(2-ethyl-4-(2-bromophenyl)indenyl)}zirconium dichloride,
rac-dimethylsilylene-bis{1-(2-ethyl-4-(3-bromophenyl)indenyl)}zirconium dichloride,
rac-dimethylsilylene-bis{1-(2-ethyl-4-(4-bromophenyl)indenyl)}zirconium dichloride,
rac-dimethylsilylene-bis{1-(2-ethyl-4-(4-biphenylyl)indenyl)}zirconium dichloride,
rac-dimethylsilylene-bis{1-(2-ethyl-4-(4-trimethylsilylphenyl)indenyl)}zirconium dichloride,
rac-dimethylsilylene-bis{1-(2-n-propyl-4-phenylindenyl)}zirconium dichloride,
rac-dimethylsilylene-bis{1-(2-n-propyl-4-(α-naphthyl)indenyl)}zirconium dichloride,
rac-dimethylsilylene-bis{1-(2-n-propyl-4-(β-naphthyl)indenyl)}zirconium dichloride,
rac-dimethylsilylene-bis{1-(2-n-propyl-4-(2-methyl-1-naphthyl)indenyl)}zirconium dichloride,
rac-dimethylsilylene-bis{1-(2-n-propyl-4-(5-acenaphthyl)indenyl)}zirconium dichloride, rac-dimethylsilylene-bis{1-(2-n-propyl-4-(9-anthryl)indenyl)}zirconium dichloride,
rac-dimethylsilylene-bis{1-(2-n-propyl-4-(9-phenanthryl)indenyl)}zirconium dichloride,
rac-dimethylsilylene-bis{1-(2-i-propyl-4-phenylindenyl)}zirconium dichloride,
rac-dimethylsilylene-bis{1-(2-i-propyl-4-(α-naphthyl)indenyl)}zirconium dichloride,
rac-dimethylsilylene-bis{1-(2-i-propyl-4-(β-naphthyl)indenyl)}zirconium dichloride,
rac-dimethylsilylene-bis{1-(2-i-propyl-4-(8-methyl-9-naphthyl)indenyl)}zirconium dichloride,
rac-dimethylsilylene-bis{1-(2-i-propyl-4-(5-acenaphthyl)indenyl)}zirconium dichloride,
rac-dimethylsilylene-bis{1-(2-i-propyl-4-(9-anthryl)indenyl)}zirconium dichloride,
rac-dimethylsilylene-bis{1-(2-i-propyl-4-(9-phenanthryl)indenyl)}zirconium dichloride,
rac-dimethylsilylene-bis{1-(2-s-butyl-4-phenylindenyl)}zirconium dichloride,
rac-dimethylsilylene-bis{1-(2-s-butyl-4-(α-naphthyl)indenyl)}zirconium dichloride,
rac-dimethylsilylene-bis{1-(2-s-butyl-4-(β-naphthyl)indenyl)}zirconium dichloride,
rac-dimethylsilylene-bis{1-(2-s-butyl-4-(2-methyl-1-naphthyl)indenyl)}zirconium dichloride,
rac-dimethylsilylene-bis{1-(2-s-butyl-4-(5-acenaphthyl)indenyl)}zirconium dichloride,
rac-dimethylsilylene-bis{1-(2-s-butyl-4-(9-anthryl)indenyl)} zirconium dichloride,
rac-dimethylsilylene-bis{1-(2-s-butyl-4-(9-phenanthryl)indenyl)}zirconium dichloride,
rac-dimethylsilylene-bis{1-(2-n-pentyl-4-phenylindenyl)}zirconium dichloride,
rac-dimethylsilylene-bis{1-(2-n-pentyl-4-(α-naphthyl)indenyl)}zirconium dichloride,
rac-dimethylsilylene-bis{1-(2-n-butyl-4-phenylindenyl)}zirconium dichloride,
rac-dimethylsilylene-bis{1-(2-n-butyl-4-(α-naphthyl)indenyl)}zirconium dichloride,
rac-dimethylsilylene-bis{1-(2-n-butyl-4-(β-naphthyl)indenyl)}zirconium dichloride,
rac-dimethylsilylene-bis{1-(2-n-butyl-4-(2-methyl-1-naphthyl)indenyl)}zirconium dichloride,
rac-dimethylsilylene-bis{1-(2-n-butyl-4-(5-acenaphthyl)indenyl)}zirconium dichloride,
rac-dimethylsilylene-bis{1-(2-n-butyl-4-(9-anthryl)indenyl)} zirconium dichloride,
rac-dimethylsilylene-bis{1-(2-n-butyl-4-(9-phenanthryl)indenyl)}zirconium dichloride,
rac-dimethylsilylene-bis{1-(2-i-butyl-4-phenylindenyl)}zirconium dichloride,
rac-dimethylsilylene-bis{1-(2-i-butyl-4-(α-naphthyl)indenyl)}zirconium dichloride,
rac-dimethylsilylene-bis{1-(2-i-butyl-4-(β-naphthyl)indenyl)}zirconium dichloride,
rac-dimethylsilylene-bis{1-(2-i-butyl-4-(2-methyl-1-naphthyl)indenyl)}zirconium dichloride,
rac-dimethylsilylene-bis{1-(2-i-butyl-4-(5-acenaphthyl)indenyl)}zirconium dichloride,
rac-dimethylsilylene-bis{1-(2-i-butyl-4-(9-anthryl)indenyl)} zirconium dichloride,
rac-dimethylsilylene-bis{1-(2-i-butyl-4-(9-phenanthryl)indenyl)}zirconium dichloride,
rac-dimethylsilylene-bis{1-(2-neopentyl-4-phenylindenyl)}zirconium dichloride,
rac-dimethylsilylene-bis{1-(2-neopentyl-4-(α-naphthyl)indenyl)}zirconium dichloride,
rac-dimethylsilylene-bis{1-(2-n-hexyl-4-phenylindenyl)} zirconium dichloride,
rac-dimethylsilylene-bis{1-(2-n-hexyl-4-(α-naphthyl)indenyl)}zirconium dichloride,
rac-methylphenylsilylene-bis{1-(2-ethyl-4-phenylindenyl)} zirconium dichloride,
rac-methylphenylsilylene-bis{1-(2-ethyl-4-(α-naphthyl)indenyl)}zirconium dichloride,
rac-methylphenylsilylene-bis{1-(2-ethyl-4-(9-anthryl)indenyl)}zirconium dichloride,
rac-methylphenylsilylene-bis{1-(2-ethyl-4-(9-phenanthryl)indenyl)}zirconium dichloride,
rac-diphenylsilylene-bis{1-(2-ethyl-4-phenylindenyl)}zirconium dichloride,
rac-diphenylsilylene-bis{1-(2-ethyl-4-(α-naphthyl)indenyl)} zirconium dichloride,
rac-diphenylsilylene-bis{1-(2-ethyl-4-(9-anthryl)indenyl)} zirconium dichloride,
rac-diphenylsilylene-bis{1-(2-ethyl-4-(9-phenanthryl)indenyl)}zirconium dichloride,
rac-diphenylsilylene-bis{1-(2-ethyl-4-(4-biphenylyl)indenyl)}zirconium dichloride,
rac-methylene-bis{1-(2-ethyl-4-phenylindenyl)}zirconium dichloride,
rac-methylene-bis{1-(2-ethyl-4-(α-naphthyl)indenyl)}zirconium dichloride,
rac-ethylene-bis{1-(2-ethyl-4-phenylindenyl)}zirconium dichloride,
rac-ethylene-bis{1-(2-ethyl-4-(α-naphthyl)indenyl)}zirconium dichloride,
rac-ethylene-bis{1-(2-n-propyl-4-(α-naphthyl)indenyl)}zirconium dichloride,
rac-dimethylgermyl-bis{1-(2-ethyl-4-phenylindenyl)}zirconium dichloride,
rac-dimethylgermyl-bis{1-(2-ethyl-4-(α-naphthyl)indenyl)} zirconium dichloride, and
rac-dimethylgermyl-bis{1-(2-n-propyl-4-phenylindenyl)} zirconium dichloride.

Moreover, examples of the transition metal compound represented by the above general formula (I-4) also include the aforementioned compounds, zirconium of which is substituted with titanium or hafnium. In the present embodiment, a racemate of the transition metal compound represented by the above general formula (I-4) is generally used as a catalytic component, and an R-form or an S-form thereof can also be used.

Such a transition metal compound represented by the general formula (I-4) can be produced in accordance with Journal of Organometallic Chem. 288 (1985), pp. 63 to 67, and European Patent Application Laid-Open No. 0,320,762, specification and examples.

The transition metal compound (II) having an annular η-binding anionic ligand is, for example, a transition metal compound represented by the following general formula (II-1):

$$L_lMX_pX'_q \qquad \text{(II-1)}$$

In the above formula, M represents a transition metal of group 4 of the long format periodic table, having oxidation number of +2, +3 and +4, which is $\eta^5$ bound to one or more ligands L, and this transition metal is particularly preferably titanium.

In the above formula, L represents an annular η-binding anionic ligand(s), and each independently represents a cyclopentadienyl group, an indenyl group, a tetrahydroindenyl group, a fluorenyl group, a tetrahydrofluorenyl group, or an octahydrofluorenyl group, and these groups may optionally have 1 to 8 substituents each independently selected from a hydrocarbon group comprising 20 or less non-hydrogen atoms, halogen, a halogen-substituted hydrocarbon group, an aminohydrocarbyl group, a hydrocarbyloxy group, a dihydrocarbylamino group, a dihydrocarbylphosphino group, a silyl group, an aminosilyl group, a hydrocarbyloxysilyl group, and a halosilyl group.

In the above formula, when 1 is 2, the two ligands L may be bound by a divalent substituent, such as hydrocarbadiyl comprising 20 or less non-hydrogen atoms, halohydrocarbadiyl, hydrocarbyleneoxy, hydrocarbyleneamino, siladiyl, halosiladiyl, or aminosilane.

In the above formula, X each independently represents a monovalent anionic σ-bound ligand having 60 or less non-hydrogen atoms, a divalent anionic σ-bound ligand divalently binding to M, or a divalent anion σ-bound ligand binding at a valence of 1 to each of M and L.

X' each independently represents a neutral Lewis base coordination compound selected from phosphine containing 4 to 40 carbon atoms, ether, amine, olefin, and/or conjugated diene.

In the above formula, "1" represents an integer of 1 or 2. p represents an integer of 0, 1 or 2, and when X is a monovalent anionic σ-bound ligand or a divalent anionic σ-bound ligand binding at a valence of 1 to each of M and L, p is "1" or more fewer than the format oxidation number of M, or when X is a divalent anionic σ-bound ligand divalently binding to M, p is "1"+1 or more fewer than the format oxidation number of M. In addition, q is 0, 1 or 2. The transition metal compound is preferably represented by the above formula (1), in which l=1.

For example, a preferred example of the transition metal compound is represented by the following formula (II-2):

(II-2)

In the above formula, M is titanium, zirconium or hafnium having a format oxidation number of +2, +3 or +4, and it is particularly preferably titanium.

In the above formula, $R^{16}$ each independently represents hydrogen, a hydrocarbon group, a silyl group, a germyl group, a cyano group, halogen, or a complex group thereof, and each group can have 20 or less non-hydrogen atoms.

Moreover, the groups $R^{16}$ adjacent to each other may form a divalent derivative such as hydrocarbadiyl, siladiyl, or germadiyl, so that they may be annular.

X" each independently represents halogen, a hydrocarbon group, a hydrocarbyloxy group, a hydrocarbylamino group or a silyl group, and each group has 20 or less non-hydrogen atoms. In addition, two groups X" may form neutral conjugated diene containing 5 to 30 carbon atoms, or a divalent derivative. In the above formula, Y represents —O—, —S—, —NR*— or —PR*—, and Z represents $SiR^*_2$, $CR^*_2$, $SiR^*_2SiR^*_2$, $CR^*_2CR^*_2$, $CR^*\!=\!CR^*$, $CR^*_2SiR^*_2$ or $GeR^*_2$, wherein "R*" each independently represents an alkyl group containing 1 to 12 carbon atoms, or an aryl group. In addition, n represents an integer of 1 to 3.

Furthermore, a more preferred example of the transition metal compound is represented by the following formula (II-3) or the following formula (II-4):

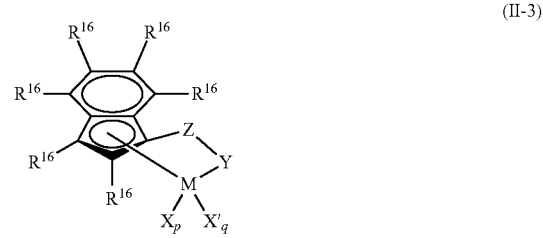

(II-3)

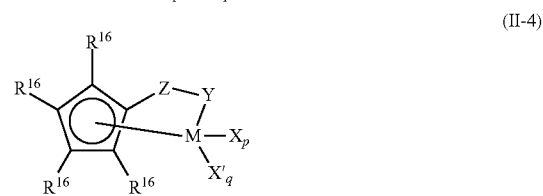

(II-4)

In the above formula, $R^{16}$ each independently represents hydrogen, a hydrocarbon group, a silyl group, a germyl group, a cyano group, halogen or a complex group thereof, and each group can have 20 or less non-hydrogen atoms. In addition, the transition metal M is titanium, zirconium or hafnium, and titanium is preferable.

Z, Y, X and X' are defined above. p is 0,1 or 2, and q is 0 or 1. When p is 2 and q is 0, the oxidation number of M is +4, and X represents halogen, a hydrocarbon group, a hydrocarbyloxy group, a dihydrocarbylamino group, a dihydrocarbylphosphide group, a hydrocarbylsulfide group, a silyl group or a complex group thereof, and each group has 20 or less non-hydrogen atoms.

Moreover, when p is 1 and q is 0, the oxidation number of M is +3, and X represents a stabilized anion ligand selected from an allyl group, a 2-(N,N-dimethylaminomethyl)phenyl group and a 2-(N,N-dimethyl)-aminobenzyl group, or the oxidation number of M is +4, and X represents a divalent conjugated diene derivative, or both M and X form a metallocyclopentene group.

Furthermore, when p is 0 and q is 1, the oxidation number of M is +2, and X' represents a neutral conjugated or non-conjugated diene, which may be optionally substituted one or more hydrocarbons, and the X' can comprise 40 or less carbon atoms and forms a π-type complex with M.

Further, in the present invention, the most preferred example of the transition metal compound is represented by the following formula (II-5) and the following formula (II-6):

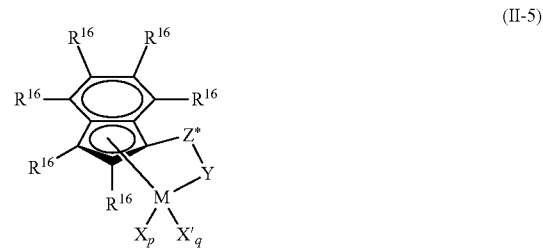

(II-5)

-continued

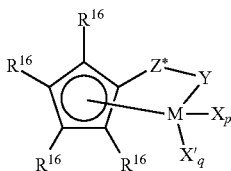

(II-6)

In the above formula, $R^{16}$ each independently represents hydrogen or an alkyl group containing 1 to 6 carbon atoms. In addition, M represents titanium, Y represents —O—, —S—, —NR*— or —PR*—, and Z* represents SiR*$_2$, CR*$_2$, SiR*$_2$SiR*$_2$, CR*$_2$CR*$_2$, CR*=CR*, CR*$_2$SiR$_2$ or GeR*$_2$, wherein R* each independently represents hydrogen, or a hydrocarbon group, a hydrocarbyloxy group, a silyl group, a halogenated alkyl group, a halogenated aryl group or a complex group thereof. The R* can have 20 or less non-hydrogen atoms, and further, as necessary, two groups R* in Z*, or R* in Z* and R* in Y may be annular.

In addition, p is 0, 1 or 2, and q is 0 or 1. When p is 2 and q is 0, the oxidation number of M is +4, and X each independently represents a methyl group or a hydrobenzyl group. When p is 1 and q is 0, the oxidation number of M is +3, and X represents a 2-(N,N-dimethyl)-aminobenzyl group, or the oxidation number of M is +4, and X represents 2-butene-1,4-diyl.

Moreover, when p is 0 and q is 1, the oxidation number of M is +2, and X' represents 1,4-diphenyl-1,3-butadiene or 1,3-pentadiene. The dienes exemplify asymmetric dienes that form a metal complex, and they are actually a mixture of individual geometric isomers.

[(B) Mesoporous Structure Compound]

In the present embodiment, a mesoporous structure compound is preferably used as a catalyst carrier.

In the present embodiment, the term "mesoporous structure compound" is used to mean an inorganic substance comprising pores having opening portions with a diameter of 1.5 nm to 10 nm, which are aligned with certain regularity on the surface, and a representative example of such a mesoporous structure compound is mesoporous silica.

The mesoporous structure compound used in the present embodiment has a pore size of 1.5 nm or more and 10 nm or less, and preferably 1.7 nm or more and 4.5 nm or less. In addition, the present mesoporous structure compound is preferably a porous solid having almost uniform pore size. The mesoporous structure compound preferably has, for example, a honeycomb structure, in which the opening portions of pores are regularly aligned in an identical direction.

As such a mesoporous structure compound, a conventionally known compound can be used. For example, as a mesoporous structure compound comprising silica as a main component, FSM-16 produced by inserting quaternary ammonium salts between the layers of sheet silicate has been reported in Bulletin of Chemical Society of Japan (Bull. Chem. Soc. Jpn.), Vol. 63, p. 988, 1990. Moreover, MCM41 produced by polymerization of silicic acid using quaternary ammonium salts as an organic auxiliary agent has been reported in Nature, Vol. 359, p. 710, 1992. Furthermore, a spherical mesoporous structure compound produced in accordance with the specification and examples of Japanese Patent No. 3410634 has also been reported.

Further, a mesoporous structure compound, in which the outer surface of the pore wall of each mesopore is selectively modified with an organic group and the inner surface of the mesopore is selectively used as a reaction field, has been reported in the specification and examples of Japanese Patent No. 5563846.

As mesoporous structure compounds having pores with a pore size of 1.5 nm to 10 nm, other than silica, zirconium phosphate salts produced using quaternary ammonium salts as a template have been reported in Advanced Materials (Adv. Mater.), Vol. 10, p. 812, 1998. In addition, aluminum phosphate salts produced using alkylamine as an organic auxiliary agent have been reported in Chemical Communication (Chem. Commun.), p. 1009, 1997.

It is to be noted that some structure-forming elements of the mesoporous structure compound produced by the aforementioned method may be substituted with other metal elements, as long as the structure of the compound is maintained.

More specific examples of the method for producing the mesoporous structure compound include: a method for producing the mesoporous structure compound, which comprises hydrolyzing metal alkoxide such as tetraethoxysilane using alkylamine as an organic auxiliary agent and then calcining the obtained product at a temperature of 500° C. to 800° C.; a method for producing the mesoporous structure compound, which comprises inserting quaternary ammonium salts between the layers of a layered compound such as kanemite, followed by hydrothermal synthesis, and then calcining the obtained product at a temperature of 500° C. to 800° C.; and a method for producing the mesoporous structure compound, which comprises subjecting colloid-state silica such as colloidal silica or water glass using quaternary ammonium salts as a template, followed by hydrothermal synthesis, and then calcining the obtained product at a temperature of 500° C. to 800° C. It is to be noted that the methods for producing the mesoporous structure compound are not limited to the aforementioned production methods, as long as the methods comply with the purpose of the present embodiment.

When a mesoporous structure compound is produced by the aforementioned method, the pore size of the mesoporous structure compound depends on the molecular size of alkylamine or quaternary ammonium salts, which are used upon the production of the compound. In order to produce a mesoporous structure compound having a pore size of 1.5 nm to 10 nm, alkylamine or quaternary ammonium salts, having a straight-chain alkyl group containing 6 to 24 carbon atoms, are preferably used, and further, alkylamine or quaternary ammonium salts, having a straight-chain alkyl group containing 8 to 20 carbon atoms, are particularly preferably used.

The properties of the mesoporous structure compound used in the present invention are different depending on the type and the production method thereof. A preferably used mesoporous structure compound desirably has a particle diameter of 0.1 to 300 μm and preferably 1 to 50 μm, a specific surface area that is in a range of 50 to 1000 m$^2$/g and preferably 200 to 900 m$^2$/g, and a pore volume that is in a range of 0.3 to 3.0 cm$^3$/g and preferably 0.5 to 2.0 cm$^3$.

[(C) Co-catalyst]

In the present embodiment, a co-catalyst may be used, as necessary. The type of the co-catalyst is not particularly limited, and the co-catalyst is, for example, at least one compound selected from (C-1) an organic metal compound, (C-2) an organic aluminum oxy compound, and (C-3) a compound reacting with (A) the transition metal compound to form an ion pair.

(C-1) Organic Metal Compound

Specific examples of (C-1) the organic metal compound, which is used in the present embodiment, as necessary, include the following organic metal compounds of groups 1 and 2 and groups 12 and 13 of the periodic table.

(C-1a) Organic Aluminum Compound Represented by the General Formula: $R^a_m Al(OR^b)_n H_p X_q$, wherein $R^a$ and $R^b$, which may be the same or different, each represent a hydrocarbon group containing 1 to 15, and preferably 1 to 4 carbon atoms, X represents a halogen atom, m is a number of $0<m\leq3$, n is a number of $0\leq n<3$, p is a number of $0\leq p<3$, and q is a number of $0\leq q<3$, wherein $m+n+p+q=3$).

(C-1b) Complex Alkylation Product of Metal of Group 1 of the Periodic Table and Aluminum, Represented by the General Formula: $M^2 AlR^a_4$, wherein $M^2$ represents Li, Na or K, and $R^a$ represents a hydrocarbon group containing 1 to 15, and preferably 1 to 4 carbon atoms.

(C-1c) Dialkyl Compound of Group 2 or Group 12 of the Periodic Table, Represented by the General Formula: $R^a R^b M^3$, wherein $R^a$ and $R^b$, which may be the same or different, each represent a hydrocarbon group containing 1 to 15, and preferably 1 to 4 carbon atoms, and $M^3$ represents Mg, Zn or Cd.

Examples of the organic aluminum compound (C-1a) include the following compounds.

An organic aluminum compound represented by the general formula: $R^a_m Al(OR^b)_{3-m}$, wherein $R^a$ and $R^b$, which may be the same or different, each represent a hydrocarbon group containing 1 to 15, and preferably 1 to 4 carbon atoms, and m is preferably a number of $1.5 \leq m \leq 3$.

An organic aluminum compound represented by the general formula: $R^a_m AlX_{3-m}$, wherein $R^a$ represents a hydrocarbon group containing 1 to 15, and preferably 1 to 4 carbon atoms, X represents a halogen atom, and m is preferably $0<m<3$.

An organic aluminum compound represented by the general formula: $R^a_m AlH_{3-m}$, wherein $R^a$ represents a hydrocarbon group containing 1 to 15, and preferably 1 to 4 carbon atoms, and m is preferably $2 \leq m < 3$.

An organic aluminum compound represented by the general formula: $R^a_m Al(OR^b)_n X_q$, wherein $R^a$ and $R^b$, which may be the same or different, each represent a hydrocarbon group containing 1 to 15, and preferably 1 to 4 carbon atoms, X represents a halogen atom, m is a number of $0<m\leq3$, n is a number of $0\leq n<3$, and q is a number of $0\leq q<3$, wherein $m+n+q=3$.

More specific examples of the aforementioned organic aluminum compound (C-1a) include:

tri(n-alkyl)aluminums, such as trimethylaluminum, triethylaluminum, tri(n-butyl)aluminum, tripropylaluminum, tripentylaluminum, trihexylaluminum, trioctylaluminum, and tridecylaluminum; tri-branched chain alkylaluminums, such as triisopropylaluminum, triisobutylaluminum, tri(sec-butyl)aluminum, tri(tert-butyl)aluminum, tri(2-methylbutyl)aluminum, tri(3-methylbutyl)aluminum, tri(2-methylpentyl)aluminum, tri(3-methylpentyl)aluminum, tri(4-methylpentyl)aluminum, tri(2-methylhexyl)aluminum, tri(3-methylhexyl)aluminum, and tri(2-ethylhexyl)aluminum;

tricycloalkylaluminums, such as tricyclohexylaluminum and tricyclooctylaluminum; triarylaluminums, such as triphenylaluminum and tritolylaluminum; dialkylaluminum hydrides such as diisobutylaluminum hydride;

trialkenylaluminums such as triisoprenylaluminum represented by $(i-C_4H_9)_x Al_y (C_5H_{10})_z$ (wherein x, y and z each represent a positive number, and $z \geq 2x$);

alkylaluminum alkoxides, such as isobutylaluminum methoxide, isobutylaluminum ethoxide, and isobutylaluminum isopropoxide;

dialkylaluminum alkoxides, such as dimethylaluminum methoxide, diethylaluminum ethoxide, and dibutylaluminum butoxide; alkylaluminum sesquialkoxides, such as ethylaluminum sesquiethoxide and butylaluminum sesquibutoxide;

partially alkoxylated alkylaluminums having an average composition, for example, represented by $R^a_{2.5} Al(OR^b)_{0.5}$;

dialkylaluminum aryloxides, such as diethylaluminum phenoxide, diethylaluminum (2,6-di-t-butyl-4-methylphenoxide), ethylaluminum bis(2,6-di-t-butyl-4-methylphenoxide), diisobutylaluminum (2,6-di-t-butyl-4-methylphenoxide), and isobutylaluminum bis(2,6-di-t-butyl-4-methylphenoxide);

dialkylaluminum halides, such as dimethylaluminum chloride, diethylaluminum chloride, dibutylaluminum chloride, diethylaluminum bromide, and diisobutylaluminum chloride;

alkylaluminum sesquihalides, such as ethylaluminum sesquichloride, butylaluminum sesquichloride, and ethylaluminum sesquibromide; partially halogenated alkylaluminums including alkylaluminum dihalides, such as ethylaluminum dichloride, propylaluminum dichloride, and butylaluminum dibromide;

dialkylaluminum hydrides, such as diethylaluminum hydride and dibutylaluminum hydride;

other partially hydrogenated alkylaluminums including alkylaluminum dihydrides, such as ethylaluminum dihydride and propylaluminum dihydride; and partially alkoxylated and halogenated alkylaluminums, such as ethylaluminum ethoxy chloride, butylaluminum butoxy chloride, and ethylaluminum ethoxy bromide.

(C-2) Organic Aluminum Oxy Compound

Examples of the organic aluminum oxy compound (C-2) include annular aluminoxane having a structure represented by the general formula: $\{-Al(R)-O-\}_j$, and linear aluminoxane having a structure represented by the general formula: $R\{-Al(R)-O-\}_k AlR_2$. Specific examples of the R include alkyl groups such as a methyl group, an ethyl group, an n-propyl group, an isopropyl group, an n-butyl group, an isobutyl group, an n-pentyl group, and a neopentyl group. In addition, there may be multiple types of R in a single molecule. Moreover, j represents an integer of 2 or greater, and k represents an integer of 1 or greater. R is preferably a methyl group or an isobutyl group, j is an integer of 2 to 40, and k is an integer of 1 to 40.

The aforementioned aluminoxane is produced by various types of methods. The production method is not particularly limited, and a known method may be applied. For example, aluminoxane is produced by dissolving trialkylaluminum (e.g., trimethylaluminum, etc.) in a suitable organic solvent (aromatic hydrocarbon such as benzene, an aliphatic hydrocarbon such as hexane, etc.) to obtain a solution, and then allowing the obtained solution to come into contact with water. Alternatively, there can also be applied a production method comprising allowing trialkylaluminum (e.g., trimethylaluminum, etc.) to come into contact with metal salts comprising crystallization water (e.g., copper sulfate hydrate, etc.). The thus obtained aluminoxane is generally considered to be a mixture of an annular structure and a linear structure.

(C-3) Compound Reacting with (A) the Transition Metal Compound to Form an Ion Pair Examples of (C-3) the compound reacting with (A) the transition metal compound to form an ion pair (hereinafter referred to as an "ionized ionic compound"), which is used in the present embodiment, as necessary, include Lewis acid, an ionic compound, a borane compound, and a carborane compound, which are described in Japanese Patent Laid-Open No. 1-501950, Japanese Patent Laid-Open No. 1-502036, Japanese Patent Laid-Open No. 3-179005, Japanese Patent Laid-Open No. 3-179006, Japanese Patent Laid-Open No. 3-207703, Japanese Patent Laid-Open No. 3-207704, U.S. Pat. No. 5,321,106, and the like.

Specifically, an example of the Lewis acid is a compound represented by $BR^{18}{}_3$ (wherein $R^{18}$ represents a phenyl group optionally having a substituent such as fluorine, a methyl group or a trifluoromethyl group, or fluorine). Specific examples of the Lewis acid include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron, and tris(3,5-dimethylphenyl)boron.

An example of the ionic compound is a compound represented by the following general formula (III):

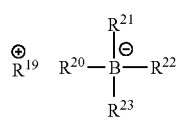

(III)

In the above formula, $R^{19}$ represents $H^+$, a carbonium cation, an oxonium cation, an ammonium cation, a phosphonium cation, a cycloheptyltrienyl cation, a ferrocenium cation having a transition metal, or the like. $R^{20}$ to $R^{23}$, which may be the same or different, each represent an organic group, and preferably, an aryl group or a substituted aryl group.

Specific examples of the above described carbonium cation include trisubstituted carbonium cations such as a triphenylcarbonium cation, a tri(methylphenyl)carbonium cation, and a tri(dimethylphenyl)carbonium cation.

Specific examples of the above described oxonium cation include a diphenyloxonium cation, a di(o-tolyl)oxonium cation, and a di(2,6-dimethylphenyl)oxonium cation.

Specific examples of the above described ammonium cation include:
trialkylammonium cations, such as a trimethylammonium cation, a triethylammonium cation, a tripropylammonium cation, a tributylammonium cation, and a tri(n-butyl)ammonium cation;
N,N-dialkylanilinium cations, such as an N,N-dimethylanilinium cation, an N,N-diethylanilinium cation, and an N,N-2,4,6-pentamethylanilinium cation; and
dialkylammonium cations, such as a di(isopropyl)ammonium cation and a dicyclohexylammonium cation.

Specific examples of the above described phosphonium cation include triarylphosphonium cations such as a triphenylphosphonium cation, a tri(methylphenyl)phosphonium cation, and a tri(dimethylphenyl)phosphonium cation.

$R^{19}$ is preferably a carbonium cation, an ammonium cation or the like, and is particularly preferably a triphenylcarbonium cation, an N,N-dimethylanilinium cation, and an N,N-diethylanilinium cation.

Moreover, examples of the ionic compound also include trialkyl-substituted ammonium salts, N,N-dialkylanilinium salts, dialkylammonium salts, and triarylphosphonium salts.

Specific examples of the trialkyl-substituted ammonium salts include:
triethylammonium tetra(phenyl)boron,
tripropylammonium tetra(phenyl)boron,
tri(n-butyl)ammonium tetra(phenyl)boron,
trimethylammonium tetra(p-tolyl)boron,
trimethylammonium tetra(o-tolyl)boron,
tri(n-butyl)ammonium tetra(pentafluorophenyl)boron,
tripropylammonium tetra(o,p-dimethylphenyl)boron,
tri(n-butyl)ammonium tetra(m,m-dimethylphenyl)boron,
tri(n-butyl)ammonium tetra(p-trifluoromethylphenyl)boron,
tri(n-butyl)ammonium tetra(3,5-ditrifluoromethylphenyl) boron, and tri(n-butyl)ammonium tetra(o-tolyl)boron.

Specific examples of the N,N-dialkylanilinium salts include:
N,N-dimethylanilinium tetra(phenyl)boron,
N,N-diethylanilinium tetra(phenyl)boron, and
N,N-2,4,6-pentamethylanilinium tetra(phenyl)boron.

Specific examples of the dialkylammonium salts include di(1-propyl)ammonium tetra(pentafluorophenyl)boron and dicyclohexylammonium tetra(phenyl)boron.

Moreover, examples of the ionic compound further include triphenylcarbenium tetrakis(pentafluorophenyl)borate, N,N-dimethylanilinium tetrakis(pentafluorophenyl)borate, ferrocenium tetra(pentafluorophenyl)borate, a triphenylcarbenium pentaphenylcyclopentadienyl complex, an N,N-diethylanilinium pentaphenylcyclopentadienyl complex, and a boron compound represented by the following formula (IV) or (V):

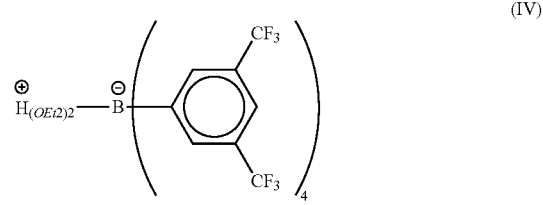

(IV)

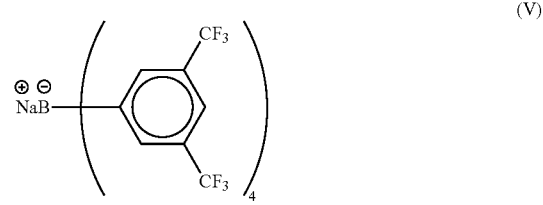

(V)

Specific examples of the borane compound include:
decaborane;
anion salts, such as bis[tri(n-butyl)ammonium] nonaborate,
bis[tri(n-butyl)ammonium] decaborate,
bis[tri(n-butyl)ammonium] undecaborate,
bis[tri(n-butyl)ammonium] dodecaborate,
bis[tri(n-butyl)ammonium] decachlorodecaborate, and
bis[tri(n-butyl)ammonium] dodecachlorododecaborate; and
metal borane anion salts, such as tri(n-butyl)ammonium bis(dodecahydridedodecaborate)cobaltate(III) and
bis[tri(n-butyl)ammonium] bis(dodecahydridedodecaborate)nickelate(III).

Specific examples of the carborane compound include: anion salts, such as
4-carbanonaborane, 9-dicarbadecaborane,
dodecahydride-1-phenyl-1,3-dicarbanonaborane,
dodecahydride-1-methyl-1,3-dicarbanonaborane,
undecahydride-1,3-dimethyl-1,3-dicarbanonaborane,
undecahydride-7,8-dimethyl-7,8-dicarbaundecaborane,
dodecahydride-11-methyl-2,7-dicarbaundecaborane,
tri(n-butyl)ammonium 1-carbadecaborate,
tri(n-butyl)ammonium 1-carbaundecaborate,
tri(n-butyl)ammonium 1-carbadodecaborate,
tri(n-butyl)ammonium 1-trimethylsilyl-1-carbadecaborate,
tri(n-butyl)ammonium bromo-1-carbadodecaborate,
tri(n-butyl)ammonium 6-carbadecaborate,
tri(n-butyl)ammonium dodecahydride-8-methyl-7,9-dicarbaundecaborate,
tri(n-butyl)ammonium undecahydride-8-ethyl-7,9-dicarbaundecaborate,
tri(n-butyl)ammonium undecahydride-8-butyl-7,9-dicarbaundecaborate,
tri(n-butyl)ammonium undecahydride-8-allyl-7,9-dicarbaundecaborate,
tri(n-butyl)ammonium undecahydride-9-trimethylsilyl-7,8-dicarbaundecaborate, and
tri(n-butyl)ammonium undecahydride-4,6-dibromo-7-carbaundecaborate; and
metal carborane anion salts, such as
tri(n-butyl)ammonium bis(nonahydride-1,3-dicarbanonaborate)cobaltate(III),
tri(n-butyl)ammonium bis(undecahydride-7,8-dicarbaundecaborate)ferrate(III),
tri(n-butyl)ammonium bis(undecahydride-7,8-dicarbaundecaborate)cobaltate(III),
tri(n-butyl)ammonium bis(undecahydride-7,8-dicarbaundecaborate)nickelate(III),
tri(n-butyl)ammonium bis(undecahydride-7,8-dicarbaundecaborate)cuprate(III),
tri(n-butyl)ammonium bis(undecahydride-7,8-dicarbaundecaborate)aurate(III),
tri(n-butyl)ammonium bis(nonahydride-7,8-dimethyl-7,8-dicarbaundecaborate)ferrate(III),
tri(n-butyl)ammonium bis(nonahydride-7,8-dimethyl-7,8-dicarbaundecaborate)chromate(III),
tri(n-butyl)ammonium bis(tribromooctahydride-7,8-dicarbaundecaborate)cobaltate(III),
tris[tri(n-butyl)ammonium] bis(undecahydride-7-carbaundecaborate)chromate(III),
bis[tri(n-butyl)ammonium] bis(undecahydride-7-carbaundecaborate)manganate(IV),
bis[tri(n-butyl)ammonium] bis(undecahydride-7-carbaundecaborate)cobaltate(III), and
bis[tri(n-butyl)ammonium] bis(undecahydride-7-carbaundecaborate)nickelate(IV).

The aforementioned (C-3) ionized ionic compound is used as a single type alone or in combination of two or more types.

[Synthesis of Catalyst]

In the ethylene polymerization method according to the present embodiment, it is preferable to use: an olefin polymerization catalyst (a solid catalyst) comprising the above described (A) transition metal compound, the above described (B) mesoporous structure compound, and as necessary, at least one compound used as the above described (C) co-catalyst, which is selected from (C-1) the organic metal compound, (C-2) the organic aluminum oxy compound, and (C-3) the ionized ionic compound; or an olefin polymerization catalyst (a liquid catalyst) comprising the above described (A) transition metal compound, and at least one compound used as the above described (C) co-catalyst, which is selected from (C-1) the organic metal compound, (C-2) the organic aluminum oxy compound, and (C-3) the ionized ionic compound.

Hereafter, a method for producing a catalyst, in which (A) the transition metal compound and as necessary, (C) the co-catalyst are supported on (B) the mesoporous structure compound, will be described. It is to be noted that the term "transition metal-containing mesoporous structure compound" is used in the present embodiment to mean a substance in which a component (A) is supported on a component (B), which is obtained by allowing (A) the transition metal compound (hereinafter also referred to as a "component (A)") to come into contact with (B) the mesoporous structure compound (hereinafter also referred to as a "component (B)").

An example of a method of supporting an ethylene polymerization catalyst on a carrier is a method which comprises first vacuum-drying the component (B) preferably in a temperature range of 0° C. to 200° C. for 1 hour to 5 hours, then allowing the component (B) to come into contact with the component (A) that has been mixed with an inactive hydrocarbon solvent, and then mixing the components in an inert gas atmosphere such as nitrogen, so as to prepare the supported ethylene polymerization catalyst. During the aforementioned operations, the component (A) may be allowed to come into contact with the component (B) in a vacuum state, and the atmosphere may be then converted to an inert gas atmosphere. Otherwise, the atmosphere may be converted to an inert gas atmosphere, and the two components may be then contacted and mixed with each other. In particular, from the viewpoint of efficiently supporting catalytic components in the pores of the mesoporous structure compound, a method of allowing the component (A) to come into contact with the component (B) in a vacuum state is appropriate. Moreover, when the components are mixed and contacted with each other, the component (C) can also be added thereto.

Furthermore, in order to capture an acidic substance that is generated when the component (A) is allowed to come into contact with the component (B), a basic substance, for example, alkylamine such as triethylamine or tributylamine can also be added.

When the component (C) is used, the order of mixing the components is arbitrarily selected. Preferably, a method which comprises previously contacting the component (A) with the component (B), and then adding the component (C) to the mixture, followed by mixing them, is applied.

After completion of the mixing and contacting, the amount of the component (A) supported on the component (B) can be adjusted, such that the amount of the transition metal atom in the component (A) can be $10^{-8}$ to $10^{-3}$ moles, and preferably $10^{-6}$ to $10^{-4}$ moles, per g of the component (B).

In the present embodiment, specific examples of the inactive hydrocarbon solvent used in the preparation of the olefin polymerization catalyst include: aliphatic hydrocarbons such as pentane, hexane, heptane, octane, decane, dodecane, and kerosene; alicyclic hydrocarbons such as cyclopentane, cyclohexane, and methylcyclopentane; aromatic hydrocarbons such as benzene, toluene and xylene; halogenated hydrocarbons such as ethylene chloride, chlorobenzene, and dichloromethane; mixtures thereof.

When (C-1) the organic metal compound is used as a component (C), the organic metal compound (C-1) is used in such an amount that the molar ratio [(C-1)/M] between (C-1) the organic metal compound and the transition metal atom (M) in the component (A) can be generally 0.1 to 100000, and preferably 0.5 to 50000. When (C-2) the organic aluminum oxy compound is used as a component (C), (C-2) the organic aluminum oxy compound is used in such an amount that the molar ratio [(C-2)/M] between the aluminum atom in (C-2) the organic aluminum oxy compound and the transition metal atom (M) in the component (A) can be generally 10 to 50000, and preferably 20 to 10000. When (C-3) the ionized ionic compound is used as a component (C), (C-3) the ionized ionic compound is used in such an amount that the molar ratio [(C-3)/M] between (C-3) the ionized ionic compound and the transition metal atom (M) in the component (A) can be generally 1 to 20, and preferably 1 to 10.

The mixing temperature applied when the above described components are mixed with one another is generally −30° C. to 130° C., and preferably −20° C. to 120° C., and the contacting time is 5 minutes to 120 hours, and preferably 30 minutes to 24 hours. In addition, the mixing temperature may be changed upon the mixing and contacting of the components.

Thereafter, a supernatant portion is removed from the slurry solution, and the remaining solid component is then filtrated and washed with a hydrocarbon solvent, and thereafter, the solid component is preferably subjected to vacuum drying.

From the viewpoint of regulating the quantity of heat of fusion ΔH, a plane orientation index ratio, and the difference in melting point before and after processing, after the component (A) has been allowed to come into contact with the component (B), the obtained mixture is preferably allowed to come into contact with a substance having the function of modifying (A) the transition metal compound. For example, the ethylene polymer of the present embodiment is preferably synthesized by performing a step of using a transition metal-containing mesoporous structure compound obtained by allowing (A) a transition metal compound to come into contact with (B) a mesoporous structure compound, and then allowing the obtained mixture to come into contact with a substance having the function of modifying (A) the transition metal compound, and further using (C) a co-catalyst, so that polymerization is carried out by using an olefin polymerization catalyst comprising the aforementioned components, although the synthetic method is not limited thereto.

The "substance having the function of modifying (A) the transition metal compound" is not particularly limited, as long as it has the property of reducing the catalytic capacity of (A) the transition metal compound. Examples of the substance having the function of modifying the component (A) include activated gas such as oxygen, water vapor, carbon monoxide, ammonia, hydrogen sulfide or ozone, gas or air comprising the same, and a bulk compound having a hydroxyl group.

By allowing the catalyst to come into contact with such a substance, the quantity of heat of fusion ΔH, a plane orientation index ratio, and the difference in melting point before and after processing can be regulated. The reason therefore has not yet been known at this stage, but it is considered that (A) the transition metal compound supported on the outer surface of a mesopore is preferentially inactivated by allowing it to come into contact with the substance having the function of modifying a catalyst species, so that the polymerization reaction inside the mesopore can be preferentially advanced. It is assumed that, by performing polymerization under such conditions, molecular chains existing in mesopores, which are restricted to move and are easily crystallized, are relatively increased, and as a result, individual physical properties can be regulated.

Furthermore, from the same viewpoint as described above, (B) a mesoporous structure compound, in which reactive points on the outer surfaces (for example, other than the inner surfaces) of the mesopores have previously been inactivated, may also be used. For example, the ethylene polymer of the present embodiment is preferably synthesized by performing a step of using a transition metal-containing mesoporous structure compound obtained by allowing (A) a transition metal compound to come into contact with (B) a mesoporous structure compound, in which reactive points on the outer surfaces of mesopores have been inactivated, and further using (C) a co-catalyst, so that polymerization is carried out by using an olefin polymerization catalyst comprising the aforementioned components, although the synthetic method is not limited thereto.

Examples of the bulk compound having a hydroxyl group include (1,3,5-trimethyl-2,4,6-tris(3',5'-di-t-butyl-4'-hydroxybenzyl)benzene, octadecyl 3-(3',5'-di-t-butyl-4'-hydroxyphenyl)propionate, and tetra3-(3',5'-di-t-butyl-4'-hydroxyphenyl)propoxybutane.

In particular, in the case of using activated gas, the time at which the activated gas is allowed to come into contact with the catalyst is preferably 0.5 minutes to 5 hours, more preferably 5 minutes to 3 hours, and further preferably 10 minutes to 1 hour. However, since the contact probability is largely changed depending on the concentration of the activated gas and the surface area of the catalyst, the optimal contacting time is determined, as appropriate.

Further, as a catalyst carrier, a mesoporous structure compound, in which the outer surfaces of the pore walls of mesopores are selectively modified with organic groups, which is described in the specification and examples of Japanese Patent No. 5563846, may also be used.

[Method for Producing Ethylene Polymer]

As a method for producing the ethylene polymer, the ethylene polymer of the present embodiment can be obtained by performing a polymerization process of using any one of a vapor phase polymerization method, a liquid phase polymerization method, and a slurry polymerization method. Examples of a polymerization solvent used in the slurry polymerization method include aromatic solvents such as toluene or xylene, and aliphatic hydrocarbons (propane, cyclohexane, isobutane, n-butane, n-pentane, isopentane, neopentane, n-hexane and n-heptane, etc.). A mixture of these solvents can also be used. From the viewpoint of increasing the molecular weight and the plane orientation index ratio, the solvent used in the polymerization process is preferably an aliphatic hydrocarbon. When the solvent used in the polymerization process is a mixed solvent, the content of an aliphatic hydrocarbon is preferably 50% by mass or more, more preferably 70% by mass or more, and further preferably 90% by mass or more.

The polymerization temperature is preferably −50° C. or higher and 100° C. or lower, more preferably −20° C. or higher and 60° C. or lower, further preferably 0° C. or higher and 50° C. or lower, and particularly preferably 10° C. or higher and 40° C. or lower. The polymerization pressure is not particularly limited, and it is, for example, 0.1 MPa or more and 9.8 MPa or less, preferably 0.3 MPa or more and 5.0 MPa or less, and more preferably 0.5 MPa or more and 2.0 MPa or less.

The polymerization reaction in the method for producing the ethylene polymer can be carried out by any one of batch, semi-continuous, and continuous methods, and the polymerization is preferably carried out by the continuous method.

Ethylene gas, a solvent, a catalyst and the like are continuously supplied into a polymerization system, and thereafter, they are continuously discharged together with the generated ethylene polymer from the reaction system, so that a partially high temperature state caused by a drastic ethylene reaction can be suppressed, and thereby, the inside of the polymerization system can be stabilized. In addition, it is preferable that ethylene gas, a solvent, a catalyst and the like, before being supplied to the polymerization reactor, are supplied to the reactor at the same temperature as that in the reactor, in order also to stabilize the inside of the system. If ethylene reacts with other components in a homogenous reaction system, generation of branches, double bonds, etc. in polymer chains is suppressed. In addition, deformation of the surfaces of ethylene polymer powders (an unprocessed ethylene polymer), which is caused by decomposition or crosslinking of the ethylene polymer, is also suppressed. Therefore, a continuous method, which achieves more uniformity of the inside of the polymerization system, is preferable. It is also possible to carry out polymerization by dividing it into two or more stages having different reaction conditions.

When the polymerization or copolymerization of ethylene is carried out using the aforementioned olefin polymerization catalyst, an ethylene polymerization catalyst is used, such that the amount of transition metal atoms in (A) the transition metal compound contained in the catalyst can be generally $10^{-10}$ to 1 mole, and preferably $10^{-8}$ to $10^{-2}$ moles per 100 ml of reaction volume. During the reaction, an organic aluminum oxy compound (component (C-2)) can be used, as necessary. In this case, desirably, the amount of the organic aluminum oxy compound is 20 to 50000 moles, preferably 100 to 3000 moles, and further preferably 300 to 1500 moles, per mole of transition metal atoms contained in (A) the transition metal compound. The ethylene polymerization catalyst may be mixed with the component (C-2) before polymerization, or these components may be independently added to the reaction system for polymerization. Moreover, in the case of batch polymerization, the catalyst may be added to the system, after addition of the component (C-2), so as to start polymerization, or the component (C-2) may be added to the system, after addition of the catalyst, so as to start polymerization. Otherwise, after addition of the catalyst and the component (C-2) to a polymerization reaction device, polymerization may be started by increasing the pressure to the above described pressure to stabilize the monomers.

West German Patent Application Laid-Open No. 3127133 describes that the molecular weight can be regulated in a suitable range by adding hydrogen as a chain-transfer agent into the polymerization system. When hydrogen is added into the polymerization system, the molar fraction of hydrogen is preferably 30 mol % or less, more preferably 0.1 mol % or more and 25 mol % or less, and further preferably 0.2 mol % or more and 20 mol % or less.

In addition, it is preferable to previously apply ultrasonic wave to the catalyst before addition of the catalyst. Dispersion of catalysts in catalyst slurry is improved by such ultrasonic wave irradiation. The ultrasonic wave irradiation may be carried out by applying ultrasonic wave at 20 kHz or more and 100 kHz or less, and more preferably 40 kHz or more and 60 kHz or less, to the catalyst, for 5 minutes to 5 hours, preferably within 24 hours, more preferably within 5 hours, and further preferably within 1 hour before addition of the catalyst.

The drying temperature applied in the method for producing the ethylene polymer is not particularly limited, and it is, for example, 60° C. or higher and 130° C. or lower, preferably 70° C. or higher and 120° C. or lower, and more preferably 80° C. or higher and 110° C. or lower.

If the drying temperature is 60° C. or higher, the drying operation can be efficiently carried out. On the other hand, if the drying temperature is 130° C. or lower, the drying operation can be carried out in a state in which a change in the higher-order structure, and decomposition or crosslinking caused by the fusion of the ethylene polymer are suppressed.

[Solid-phase Stretch-molded Product]

The molded product of the ethylene polymer of the present embodiment (for example, a stretch-molded product) is obtained by molding the aforementioned ethylene polymer according to a known method for molding ultra-high-molecular-weight ethylene polymers. In particular, the molded product of the ethylene polymer of the present embodiment is preferably subjected to solid-phase stretch processing involving rolling and stretching operations. In addition, the tensile strength of a stretch-molded product obtained by the stretch molding of the ethylene polymer of the present embodiment is preferably 3.0 GPa or more, more preferably 3.5 GPa, and particularly preferably 4.0 GPa. As conditions for the solid-phase stretch molding, known conditions described in the aforementioned Patent Literature 2 (International Publication No. WO2008/013144), Patent Literature 3 (National Publication of International Patent Application No. 2014-504311), etc. can be used without limitation, except for the use of the above described ethylene polymer. Specifically, the molding conditions preferably comprise a step of compressing the ethylene polymer, a step of rolling the ethylene polymer compressed in the step of compressing, a step of stretching the ethylene polymer rolled in the step of rolling, and a step of winding the ethylene polymer stretched in the step of stretching. The temperature during this molding operation is preferably the melting point of ethylene polymer particles or lower, and it is more preferable that the above described step of compressing and the above described step of stretching be carried out under conditions that do not increase the temperature above the melting point of the described ethylene polymer at any time point during the processing in the step of compressing and the step of stretching. However, it may also be possible to carry out molding at a temperature higher than the melting point, unless melt flow substantially takes place. Methods for evaluating the stretchability of a stretch-molded product comprising the ethylene polymer and the physical properties thereof will be described later.

[Intended Use]

Fibers obtained by the solid-phase stretch processing method of the present embodiment can be industrially applied to a wide range of products, including high-performance textiles such as various types of sport wears, bulletproof and/or protective clothes, and/or protective gloves, and various types of safety goods, various types of rope products such as tag ropes and/or mooring ropes, yacht ropes, and construction ropes, various types of braided cord products such as fishing lines and blind cables, net products such as fishing net and safety net, reinforcement materials or various types of non-woven fabrics, such as chemical filters and battery separators, curtain materials such as tents, and further, sport articles such as helmets and ski plates, speaker cones, prepregs, and reinforced fibers for composites for use in the reinforcement of concretes, etc.

EXAMPLES

Hereinafter, the present invention will be described in more detail in the following examples and comparative examples. However, these examples are not intended to limit the scope of the present invention. It is to be noted that evaluation methods and measurement methods used in the present examples are as follows.

(1) Viscosity-average Molecular Weight (Mv)

Viscosity-average molecular weight (Mv) was obtained by the following method in accordance with ISO1628-3 (2010). First, 20 mg of an ethylene polymer, which had been finely crushed in an agate mortar, was weighed into a melting tube, and the melting tube was then subjected to nitrogen substitution. Thereafter, 20 mL of decahydronaphthalene (containing 1 g/L 2,6-di-t-butyl-4-methylphenol) was added to the melting tube, and the mixture was then stirred at 150° C. for 2 hours, so that the ethylene polymer was dissolved therein. The solution was placed in a 135° C. thermostat chamber, and a fall time ($t_s$) between marked lines was measured using Cannon-Fenske viscometer (manufactured by Shibata Scientific Technology Ltd.; Product No.-100).

Likewise, with regard to samples in which the amount of the ethylene polymer was changed to 10 mg, 5 mg, and 2 mg, the fall time ($t_s$) between marked lines was measured. Moreover, as a blank, regarding a sample only comprising decahydronaphthalene (containing 2,6-di-t-butyl-4-methylphenol) and without comprising the ethylene polymer, the fall time ($t_b$) was measured.

The reduced viscosity ($\eta_{sp}/C$) of the ethylene polymer obtained according to the following Expression A was each plotted, and a linear expression was induced from the concentration (C) (unit: g/dL) and the reduced viscosity ($\eta_{sp}/C$) of the ethylene polymer, so as to obtain limiting viscosity ([η], unit: dL/g) extrapolated to concentration 0.

$$\eta_{sp}/C=(t_s/t_b-1)/0.1 \quad \text{(Expression A)}$$

Subsequently, applying the following Expression B, the viscosity-average molecular weight (Mv) was calculated using the calculated value of the above described limiting viscosity [η].

$$Mv=(5.34\times10^4)\times[\eta]^{1.49} \quad \text{(Expression B)}$$

(2) Quantity of Heat of Fusion ΔH Measured by Differential Scanning Calorimetry (DSC)

Using Perkin Elmer Pyris 1 DSC as a differential scanning calorimeter (DSC), the quantity of heat of fusion ΔH was measured. 8.3 to 8.5 mg of a measurement sample, to which heat history had been given at 110° C. for 6 hours under a reduced pressure environment of 0.1 to 0.5 kPa, was weighed using an electronic balance, and was then placed in an aluminum sample pan. This pan was covered with an aluminum cover, and was placed in the differential scanning calorimeter.

While nitrogen was purged at a flow rate of 20 mL/min, the sample and a reference sample were retained at 50° C. for 1 minute. Thereafter, the samples were heated from 50° C. to 180° C. at a heating rate of 10° C./min, and were then retained at 180° C. for 5 minutes. Thereafter, the samples were cooled to 50° C. at a cooling rate of 10° C./min. A baseline of the temperature rising DSC curve obtained during this operation was corrected, and a peak area was calculated using the analysis software Pyris software (version 7). The obtained value was divided by the mass of the sample to obtain the quantity of heat of fusion ΔH.

(3) Melting Points of Ethylene Polymer and Rolled Sheet Measured by Differential Scanning Calorimetry (DSC)

Using Perkin Elmer Pyris 1 DSC as a differential scanning calorimeter (DSC), the melting points of the ethylene polymer and a rolled sheet were measured. An unprocessed ethylene polymer after completion of the polymerization and sheets obtained by performing press processing and rolling thereon under the following conditions (1) to (3) were each weighed to 8.3 to 8.5 mg, using an electronic balance, and then, were each placed in an aluminum sample pan. This pan was covered with an aluminum cover, and was placed in the differential scanning calorimeter.

(1) 3 g of the ethylene polymer is pressed using a press molding machine at 130° C. at 11 MPa for 10 minutes.

(2) The resultant is cooled at 25° C. for 10 minutes, while maintaining the average pressure at 11 MPa.

(3) The obtained press sheet is heated at 140° C. for 3 minutes, and the resulting sheet is then compressed using a rolling mill having a temperature of 130° C. and a feeding rate of the roll of 1 m/min, to result in a stretch ratio of 6.

While nitrogen was purged at a flow rate of 20 mL/min, the sample and a reference sample were retained at 50° C. for 1 minute. Thereafter, the samples were heated from 50° C. to 180° C. at a heating rate of 10° C./min, and were then retained at 180° C. for 5 minutes. Thereafter, the samples were cooled to 50° C. at a cooling rate of 10° C./min. A peak top of the temperature rising DSC curve obtained during this operation was derived as a melting point.

(4) Analysis of 200/110 Plane Orientation Index Using X-ray Diffractometer

A measurement sample was analyzed by X-ray diffractometry. The measurement was carried out by a reflection method using X-ray diffractometer Ultima IV manufactured by Rigaku Corporation (X-ray species: Cu-Kα, output: 40 kV, 40 mA, a high-sensitive semiconductor one-dimensional detector). An aluminum-made sample cell was filled with a sufficient amount of sample, and the height of the sample was set at Rowland circle.

Peak separation and calculation of a peak area were carried out using the data processing software JADE (ver. 6) under conditions of a scanning angle range 2θ=15° to 27° and a scanning rate 2θ=4°/min. Upon the peak separation, one peak derived from amorphous substances and two peaks derived from crystals were established in the range of 2θ=15° to 27°. In a case where other crystal peaks were observed in this 2θ range, those peaks were also considered to be crystal peaks. The initial values of peak position and peak width were selected such that they could be close to the peak shape of the actually measured X-ray diffraction profile.

With regard to the expression of the peak shape, using a Gauss/Lorentz function (G/L ratio, asymmetric factor, height, position, and half-width), first, the G/L ratio, asymmetric factor, and half-width of the crystal peaks were used as floating parameters, and only the peak position was immobilized for the primary optimization. Thereafter, the total peak constituting factors of all peaks were used as floating parameters, and the secondary optimization was carried out.

A peak area, in which the peak position obtained by performing such peak separation was around 21.6°, was defined as A1 (110 plane peak area), and a peak area, in which the peak position was around 24°, was defined as A2 (200 plane peak area). A2/A1 was defined as 200/110 plane orientation index.

As samples, an unprocessed ethylene polymer after completion of the polymerization and sheets obtained by performing press processing and rolling under the following conditions (1) to (3) were used.

(1) 3 g of the ethylene polymer is pressed using a press molding machine at 130° C. at 11 MPa for 10 minutes.

(2) The resultant is cooled at 25° C. for 10 minutes, while maintaining the average pressure at 11 MPa.

(3) The obtained press sheet is heated at 140° C. for 3 minutes, and the resulting sheet is then compressed using a rolling mill having a temperature of 130° C. and a feeding rate of the roll of 1 m/min, to result in a stretch ratio of 6.

(5) Tensile Strength of Solid-phase Stretch-molded Product 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

The sheet obtained by the step of rolling was cut out, and it was then set in a tensile tester (Instron Corporation, INSTRON (registered trademark) 5564) resulting in a distance between chucks of 15 mm. Thereafter, the sheet was subjected to two continuous steps of stretching at 130° C. at a stretching rate of 30 mm/min in the same direction as rolling, so as to obtain a solid-phase stretch-molded product at a stretch ratio of 200 from the press sheet. The total stretch ratio was determined based on the mass per unit length of the film before and after stretching.

Tensile strength (breaking strength) was calculated from the stress and elongation at a breaking point, when the sheet was stretched using the above described tensile tester under conditions of a test temperature of 20° C. and a tension speed of 50 mm/min. The size of a test piece was set at 4 mm wide×70 mm high, and the distance between chucks was set at 40 mm.

(6) Stretch Processability 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

The sheet obtained by the step of rolling was cut out, and it was then set in a tensile tester (Instron Corporation, INSTRON (registered trademark) 5564) resulting in a distance between chucks of 15 mm. Thereafter, the sheet was subjected to uniaxial stretching at 130° C. at a stretching rate of 30 mm/min in the same direction as rolling. The stretching test was carried out five times, and the average measured value of tensile stress at a time point, at which the sheet was stretched to 30 times the press sheet, was evaluated as stretch processability according to the following evaluation criteria.

A: Tensile stress was less than 20 MPa.

B: Tensile stress was 20 MPa or more and less than 30 MPa.

C: Tensile stress was 30 MPa or more.

(7) Dimensional Stability 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

Three rectangular test pieces each having a long side that was in a stretching flow direction, a width of 10 mm, and a length of 120 mm were cut out from the sheet obtained by the step of rolling. The test pieces were left for 24 hours in an atmosphere of 23° C. and 50% RH. Thereafter, ten marked lines (100 mm each) were drawn at intervals of 10 mm in the length direction (MD direction) on one surface of each sample, and then, using a venire caliper with precision of 0.01 mm, an initial size between the marked lines was measured. Thereafter, the sample was left for 24 hours in a thermostat chamber, the temperature of which was set at 85° C., and was then cooled in an atmosphere of 23° C. and 50% RH. After that, the size between the marked lines was measured again. Regarding each size between the marked lines, a change percentage in the interval between the marked lines before and after heating was obtained, and an arithmetic mean value was calculated. The obtained value was defined as a dimensional change percentage before and after heating, and the dimensional change percentage was evaluated according to the following evaluation criteria.

A: Dimensional change percentage was 0.1% or less.

B: Dimensional change percentage was more than 0.1% and 0.5% or less.

C: Dimensional change percentage was more than 0.5%.

(8) Adhesion Retention 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

The sheet obtained by the step of rolling was cut out, and it was then set in a tensile tester (Instron Corporation, INSTRON (registered trademark) 5564) resulting in a distance between chucks of 15 mm. Thereafter, the sheet was subjected to two continuous steps of stretching at 130° C. at a stretching rate of 30 mm/min in the same direction as rolling, so as to obtain a solid-phase stretch-molded product at a stretch ratio of 200 from the press sheet.

Fifty test pieces each having a width of 5 mm and a length of 10 mm were cut out from the stretch-molded product. To each test piece, 5% by mass of matrix material (Prinlin B7137 AL commercially available from Henkel) was applied, and the five test pieces were then laminated and compressed at a temperature of 130° C. to 135° C. and at a pressure of 5 MPa. The thus adhered test pieces were cooled, so as to prepare ten laminated test pieces. Using Xenon Weather Meter X75 (manufactured by Suga Test Instruments Co., Ltd.), the laminated test pieces were irradiated with xenon light for 480 hours under conditions of a black panel temperature of 65° C. and a water-spraying time of 18 minutes/2 hours, and thereafter, the peeling state of the laminated test pieces was confirmed. Adhesion retention was evaluated according to the following evaluation criteria.

A: Neither peelings nor voids were generated between the layers.

B: No peelings were generated between the layers, but a few voids were generated.

C: Peelings were generated between the layers.

(9) Thickness Uniformity of Stretched Sheet 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

The sheet obtained by the step of rolling was cut out, and it was then set in a tensile tester (Instron Corporation, INSTRON (registered trademark) 5564). Thereafter, the sheet was stretched at 130° C. at a stretching rate of 90 mm/min in the same direction as rolling, so as to result in a stretch ratio of 100 from the press sheet. A test piece having a width of 5 mm and a length of 100 mm was cut out from the obtained sheet, and the thickness thereof was then measured at intervals of 15 mm in the stretching flow direction. A difference between the maximum value of the thickness and the minimum value thereof was calculated, and the thickness uniformity of the sheet was then evaluated according to the following evaluation criteria.

A: Difference in thickness was 0.03 mm or less.

B: Difference in thickness was more than 0.03 mm and 0.05 mm or less.

C: Difference in thickness was more than 0.05 mm.

(10) Strength Uniformity of Stretched Sheet 3 g of the ethylene polymer was pressed using a press molding machine at a highest temperature of 126° C. at an average pressure of 11 MPa for 10 minutes. While the pressure was maintained at 11 MPa, cooling was carried out at 25° C. for 10 minutes. The obtained press sheet was pre-heated at 140° C. for 3 minutes, and was then rolled at 130° C., using a rolling mill having a feeding rate of the roll of 1 m/min, at a stretch ratio of 6.

The sheet obtained by the step of rolling was cut out, and it was then set in a tensile tester (Instron Corporation, INSTRON (registered trademark) 5564). Thereafter, the sheet was stretched at 130° C. at a stretching rate of 90 mm/min in the same direction as rolling, so as to result in a stretch ratio of 100 from the press sheet. The size of a test piece was set at 25 mm wide×50 mm high. The stretching test was carried out 20 times, and the presence or absence of break(s) was counted in the midcourse of the stretching operation, and the breaking percentage was then evaluated as a strength unevenness of the sheet according to the following evaluation criteria.

A: Number of breaks was 1 or less in 20 times of stretching tests.

C: Number of breaks was two or more in 20 times of stretching tests.

Example 1

[Preparation of Catalyst]

As a mesoporous structure compound, "mesoporous silica MCM41" was synthesized according to the method described in J. Am. Chem. Soc., 114, P. 10834 (1992). Specifically, 40 g of water, 18.7 g of sodium silicate, and 1.2 g of sulfuric acid were added to a 500-ml beaker, and they were then stirred for 10 minutes. Thereafter, 77 g of 25% by mass of octyltrimethylammonium bromide aqueous solution was further added to the reaction mixture, and the thus obtained mixture was then left at rest for 0.5 hours. Subsequently, 20 g of water was added to the reaction mixture, and the obtained mixture was then reacted in a 500-ml autoclave at 100° C. for 144 hours. Thereafter, the content was filtrated, and a solid was then calcined at 540° C. for 4 hours to obtain MCM41.

1.2 g of the obtained MCM-41 (pore size: 3.0 nm, pore volume: 0.93 cm$^3$/g, BET specific surface area: 887 m$^2$/g, average particle diameter: 9.0 μm) was placed in a 100-mL two-neck eggplant flask, and was then subjected to vacuum drying at 30° C. for 4 hours. While the vacuum state was kept, 50 mL of dichloromethane solution of biscyclopentadienyltitanium dichloride (2.0 mmol) was added to the flask through a septum, using a syringe, and the obtained mixture was then stirred. One minute later, the flask was pressurized with nitrogen, so that the inside of the flask was converted to a nitrogen atmosphere. Thereafter, 50 mL of dichloromethane solution of triethylamine (40 mmol) was added to the flask, and the thus obtained mixture was stirred for 4 hours.

The stirring operation was terminated, and the reaction mixture was then left at rest. Thereafter, a supernatant was removed, and 50 mL of dichloromethane was then added to the flask for washing. Such decantation was carried out four times. The remaining solid was filtrated in the air, and the filtration residue was then washed with 20 ml of methylene chloride three times. The time required for the filtration and the washing was 30 minutes. The obtained solid was dried under a reduced pressure to obtain slightly yellow titanium-containing MCM-41.

This compound was subjected to pressure decomposition using a microwave decomposition device (model: ETHOS TC, manufactured by Milestone General K. K.), and the concentration of the titanium element was then measured by ICP-AES analysis (an inductively coupled plasma mass spectrometer, model: X Series X7, manufactured by Thermo Fisher Scientific) according to an internal standard method. As a result, it was confirmed that 0.52 mmol titanium atoms were supported per g of the compound.

[Polymerization]

0.05 g of the above prepared titanium-containing MCM-41 was introduced into a nitrogen-substituted 50-mL Schlenk flask in a nitrogen atmosphere. Thereafter, 10 ml of hexane and modified methyl aluminoxane (Al atom-relative concentration: 5.7 mass %/hexane) (10.4 mmol relative to Al atoms) were added to the flask in a nitrogen atmosphere, and the obtained mixture was then stirred at 30° C. for 0.5 hours to obtain activated catalyst slurry. Thereafter, the activated catalyst slurry was irradiated with ultrasonic wave at 100 kHz for 5 minutes.

800 mL of hexane was added to a 1.5-L autoclave, which had been sufficiently substituted with nitrogen, and 1.0 mL of the above described modified methyl aluminoxane was added thereto as a scavenger. The obtained mixture was stirred for 5 minutes. Thereafter, using a syringe, the above described activated catalyst slurry was introduced into the autoclave. Subsequently, the inside of the system was pressurized to 8.3 kg/cm$^2$ with ethylene, and while continuously supplying ethylene and while keeping the temperature of the autoclave at 30° C., the mixture was stirred at a constant rotation speed of 30 rpm for 2 hours.

After completion of the polymerization reaction, unreacted gas was purged. The content in the autoclave was poured into 1000 ml of acidic methanol containing 5% by mass of hydrochloric acid, and the precipitated polymer was filtrated and was then dried under a reduced pressure at 30° C. for approximately 6 hours, so as to obtain 54 g of the ethylene polymer.

The obtained ethylene polymer was evaluated according to the aforementioned methods, in terms of (1) viscosity-average molecular weight Mv, (2) the quantity of heat of fusion ΔH measured by differential scanning calorimetry (DSC), (3) specific peak analysis using an X-ray diffractometer, (4) melting point measured by DSC, (5) the tensile strength of a solid-phase stretch-molded product, (6) stretch processability, (7) dimensional stability, (8) adhesion retention, (9) the thickness uniformity of a stretched sheet, and (10) the uniformity of stretched sheet strength.

Example 2

An ethylene polymer was obtained by the same operations as those of Example 1, with the exception that filtration and washing were carried out not in the air, but in a nitrogen atmosphere, upon the preparation of a catalyst.

Example 3

An ethylene polymer was obtained by the same operations as those of Example 1, with the exceptions that, upon the preparation of a catalyst, mesoporous silica MCM41 was not used as a carrier, and 5 mL of toluene solution of 0.031 g of biscyclopentadienyltitanium dichloride was mixed with 7.6 mL of the above described modified methyl aluminoxane to prepare an activated catalyst solution, and the activated catalyst solution was then introduced into the autoclave.

Example 4

An ethylene polymer was obtained by the same operations as those of Example 1, with the exception that, upon the preparation of a catalyst, octyltrimethylammonium bromide used as a starting material for mesoporous silica MCM41 was changed to dodecylamine, so as to produce mesoporous silica having an average pore size of 1.7 nm (pore volume: 0.44 $cm^3/g$, BET specific surface area: 910 $m^2/g$, and average particle diameter: 16.0 μm).

Example 5

Upon the preparation of a catalyst, the used amount of biscyclopentadienyltitanium dichloride was set at 0.5 mmol. 0.25 mmol titanium atoms were supported per g of the obtained titanium-containing MCM-41. Except for this difference, the same operations as those of Example 1 were performed to obtain an ethylene polymer.

Example 6

Upon the preparation of a catalyst, filtration and washing were carried out not in the air, but in a nitrogen atmosphere. In addition, in the polymerization process, the modified methyl aluminoxane was changed to methyl aluminoxane (Al atom-relative concentration: 20 mass %/toluene), and the additive amount was changed to 1.8 mmol relative to Al atoms. Moreover, 400 mL of toluene was used as a solvent for the polymerization. Except for these differences, the same operations as those of Example 1 were performed to obtain an ethylene polymer.

Example 7

Upon the preparation of a catalyst, filtration and washing were carried out not in the air, but in a nitrogen atmosphere. In addition, the catalyst was irradiated with ultrasonic wave at 20 kHz for 5 minutes. Moreover, polymerization was carried out, while the stirring rotation number was kept at 300 rpm. Except for these differences, the same operations as those of Example 1 were performed to obtain an ethylene polymer.

Example 8

Upon the preparation of a catalyst, filtration and washing were carried out not in the air, but in a nitrogen atmosphere. In addition, in the polymerization process, the polymerization temperature was set at 50° C. Except for these differences, the same operations as those of Example 1 were performed to obtain an ethylene polymer.

Example 9

Upon the preparation of a catalyst, filtration and washing were carried out not in the air, but in a nitrogen atmosphere. In addition, in the polymerization process, polymerization was carried out, while the stirring rotation number was kept at 100 rpm. Except for these differences, the same operations as those of Example 1 were performed to obtain an ethylene polymer.

Example 10

An ethylene polymer was obtained by the same operations as those of Example 1, with the exception that polymerization was carried out, while the stirring rotation number was kept at 300 rpm in the polymerization process.

Example 11

An ethylene polymer was obtained by the same operations as those of Example 1, with the exception that the polymerization temperature was set at 50° C. in the polymerization process.

Example 12

An ethylene polymer was obtained by the same operations as those of Example 1, with the exception that, upon the preparation of a catalyst, the mesoporous silica prepared in Example 4 was crushed using a wet jet mill (manufactured by SUGINO MACHINE LIMITED, Star Burst (registered trademark) Mini, concentration of ethanol solvent: 5 mass %, spraying pressure: 150 MPa, 50 passes) to result in an average particle diameter of 2 μm, and the thus obtained mesoporous structure was used as a carrier.

Example 13

Upon the preparation of a catalyst, filtration and washing were carried out not in the air, but in a nitrogen atmosphere. In addition, the solvent used in the polymerization process was changed to a mixed solvent with a composition of hexane:toluene=7:3, and polymerization was carried out at a stirring rotation speed of 100 rpm. Except for these differences, the same operations as those of Example 1 were performed to obtain an ethylene polymer.

Comparative Example 1

An ethylene polymer was obtained by the same operations as those of Example 1, with the exception that 1 mmol % hydrogen was added and polymerization was then carried out in the polymerization process.

Comparative Example 2

Upon the preparation of a catalyst, filtration and washing were carried out not in the air, but in a nitrogen atmosphere. In addition, the catalyst was not irradiated with ultrasonic wave, and the stirring rotation speed was set at 950 rpm. Except for these differences, the same operations as those of Example 1 were performed to obtain an ethylene polymer.

Comparative Example 3

Upon the preparation of a catalyst, the octyltrimethylammonium bromide used as a starting material for mesoporous silica MCM41 was changed to cetyltrimethylammonium bromide, so as to produce mesoporous silica having an average pore size of 15.0 nm. Except for this difference, the same operations as those of Example 1 were performed to obtain an ethylene polymer.

Comparative Example 4

Modified methyl aluminoxane (11.9 mmol relative to Al atoms) was added to 0.025 g of the solid catalytic component A-1 described in the Examples of Japanese Patent No. 5774084 to prepare an activated slurry catalyst, and such an activated slurry catalyst was added and polymerization was carried out. Except for this difference, the same operations as those of Example 1 were performed to obtain an ethylene polymer.

Comparative Example 5

An ethylene polymer was obtained by the same operations as those of Example 1, with the exception that amorphous silica particles (manufactured by FUJI SILYSIA CHEMICAL LTD., CARiACTP-10) having no mesoporous structures were used, instead of the mesoporous silica MCM41.

Comparative Example 6

In polymerization process, the modified methyl aluminoxane was changed to methyl aluminoxane (Al atom-relative concentration: 20 mass %/toluene), and the additive amount was changed to 1.8 mmol relative to Al atoms. In addition, filtration and washing were carried out not in the air, but in a nitrogen atmosphere. Moreover, ultrasonic wave irradiation was not carried out on the catalyst. Furthermore, polymerization was carried out using 400 mL of toluene as a solvent, at a stirring rotation speed of 950 rpm. Except for these differences, the same operations as those of Example 1 were performed to obtain an ethylene polymer. The physical properties and evaluation results of the obtained ethylene polymers are shown in Table 1.

TABLE 1

| | | | | Example 1 | Example 2 | Example 3 | Example 4 | Example 5 | Example 6 | Example 7 | Example 8 | Example 9 | Example 10 |
|---|---|---|---|---|---|---|---|---|---|---|---|---|---|
| Production conditions | Catalyst | Type | | Metallocene | Metallocene | Metallocene | Metallocene | Metallocene | Metallocene | Metallocene | Metallocene | Metallocene | Metallocene |
| | | Carrier | | MCM41 | MCM41 | No | MCM41 | MCM41 | MCM41 | MCM41 | MCM41 | MCM41 | MCM41 |
| | | Pore size | nm | 3.0 | 3.0 | — | 1.7 | 3.0 | 3.0 | 3.0 | 3.0 | 3.0 | 3.0 |
| | | Supported amount | Timmol/gcat | 0.52 | 0.52 | — | 0.52 | 0.25 | 0.52 | 0.52 | 0.52 | 0.52 | 0.52 |
| | | Mean particle diameter | μm | 9 | 9 | — | 16 | 9 | 9 | 9 | 9 | 9 | 9 |
| | | Air exposure processing | Yes/No | Yes | No | — | Yes | Yes | No | No | No | No | Yes |
| | | Polymerization pressure | mpa | 0.83 | 0.83 | 0.83 | 0.83 | 0.83 | 0.83 | 0.83 | 0.83 | 0.83 | 0.83 |
| | | Polymerization temperature | °C. | 30 | 30 | 30 | 30 | 30 | 30 | 30 | 50 | 30 | 30 |
| | | Composition of polymerization solvent | | Hexane | Hexane | Hexane | Hexane | Hexane | Toluene | Hexane | Hexane | Hexane | Hexane |
| | | Hydrogen | mmol % | — | — | — | — | — | — | — | — | — | — |
| | | Stirring rotation number | rpm | 30 | 30 | 30 | 30 | 30 | 30 | 300 | 30 | 100 | 300 |
| | | Ultrasonic wave irradiation | kHz × irradiation time (min) | 100 × 5 | 100 × 5 | 100 × 5 | 100 × 5 | 100 × 5 | 100 × 5 | 20 × 5 | 100 × 5 | 100 × 5 | 100 × 5 |
| Physical properties of ethylene polymer | ΔH | | J/g | 247 | 238 | 237 | 252 | 242 | 231 | 233 | 235 | 240 | 237 |
| | Mv | | Ten thousand | 392 | 360 | 387 | 393 | 499 | 938 | 367 | 310 | 360 | 378 |
| | Plane orientation index ratio | | | 20.3 | 14.9 | 12.2 | 24 | 22 | 9.8 | 8.4 | 13.7 | 11.3 | 17.4 |
| | Difference in melting point | | °C. | 3.5 | 5.3 | 2.2 | 5.6 | 3.9 | 4.4 | 3.2 | 3.1 | 3.3 | 3.5 |
| Evaluation results | Tensile strength | | GPa | 4.1 | 3.6 | 3.7 | 3.9 | 4 | 3.1 | 3.2 | 3.4 | 3.3 | 3.1 |
| | Stress upon 30-fold stretching (stretch processability) | | | A | A | A | A | A | B | B | A | A | A |
| | Dimensional stability | | | A | B | B | A | B | B | B | B | A | A |
| | Adhesion retention | | | A | A | A | A | A | B | B | A | B | A |
| | Thickness uniformity of stretched sheet | | | A | A | A | A | A | B | B | A | A | A |

TABLE 1-continued

| | | | Example 11 | Example 12 | Example 13 | Comparative Example 1 | Comparative Example 2 | Comparative Example 3 | Comparative Example 4 | Comparative Example 5 | Comparative Example 6 |
|---|---|---|---|---|---|---|---|---|---|---|---|
| | | Uniformity of strength | A | A | C | A | A | A | A | A | A | A |
| Production conditions | Catalyst | Type | Metallocene | Metallocene | Metallocene | Metallocene | Metallocene | Metallocene | Ziegler-Natta | Metallocene | Metallocene |
| | | Carrier | MCM41 | MCM41 (crushed) | MCM41 | MCM41 | MCM41 | MCM41 | MgCl2 | Amorphous silica | MCM41 |
| | | Pore size | nm | 3.0 | 1.8 | 3.0 | 3.0 | 3.0 | 15 | — | — | 3.0 |
| | | Supported amount | Ti mmol/gcat | 0.52 | 0.53 | 0.52 | 0.52 | 0.52 | | 0.6 | 0.07 | 0.52 |
| | | Mean particle diameter | μm | 9 | 2 | 9 | 9 | 9 | | 7 | 5 | 9 |
| | | Air exposure processing | Yes/No | Yes | Yes | No | Yes | No | Yes | No | Yes | No |
| | | Polymerization pressure | mpa | 0.83 | 0.83 | 0.83 | 0.83 | 0.83 | 0.83 | 0.83 | 0.83 | 0.83 |
| | | Polymerization temperature | °C. | 50 | 30 | 30 | 30 | 30 | 30 | 30 | 30 | 30 |
| | | Composition of polymerization solvent | | Hexane | Hexane | Hexane:toluene = 70:30 | Hexane | Hexane | Hexane | Hexane | Hexane | Toluene |
| | | Hydrogen | mmol % | — | — | — | 1 | — | — | — | — | — |
| | | Stirring rotation number | rpm | 30 | 30 | 100 | 30 | 950 | 30 | 30 | 30 | 950 |
| | | Ultrasonic wave irradiation | kHz × irradiation time (min) | 100 × 5 | 100 × 5 | 100 × 5 | 100 × 5 | No | 100 × 5 | 100 × 5 | 100 × 5 | No |
| Physical properties of ethylene polymer | ΔH | J/g | 234 | 244 | 232 | 235 | 231 | 198 | 213 | 212 | 225 |
| | Mv | Ten thousand | 370 | 380 | 500 | 200 | 305 | 247 | 350 | 348 | 240 |
| | Plane orientation index ratio | | 17.2 | 27 | 10.9 | 13 | 5.7 | 6.8 | 3.9 | 6.2 | 6.6 |
| | Difference in melting point | °C. | 3.5 | 4.2 | 3.1 | 3.1 | 1.9 | 0.8 | 0.4 | 1.8 | 2 |
| Evaluation results | Tensile strength | GPa | 3.2 | 3.4 | 4 | 1.5 | 3.5 | Broken | Broken | Broken | 2.1 |
| | Stress upon 30-fold stretching (stretch processability) | | A | A | B | A | A | C | B | B | B |
| | Dimensional stability | | A | A | B | B | C | C | C | C | C |
| | Adhesion retention | | A | A | B | B | C | C | C | C | C |
| | Thickness uniformity of stretched sheet | | A | A | B | B | C | C | C | C | C |
| | Uniformity of strength | | A | A | A | A | C | C | C | C | C |

In Examples 1, 4, 5, and 10 to 12, a mesoporous structure compound was used as a catalyst carrier, and the processing was carried out in the air. The plane orientation index ratio of each of the obtained ethylene polymers became an extremely high value that was 16 or greater, and the properties thereof were also extremely good.

Among others, in Examples 4 and 12, a mesoporous structure compound having a smaller pore size was used. It was confirmed that ΔH was increased in this case.

In Examples 2, 6 to 9, and 13, a mesoporous structure compound was used as a catalyst carrier, but the processing was not carried out in the air. In the case of the thus obtained ethylene polymers, by appropriately combining the following conditions: to decrease the polymerization temperature, to use an aliphatic hydrocarbon as a solvent, to decrease the stirring rotation number, and to carry out ultrasonic wave irradiation, their plane orientation index ratio became a high value that was 7 or greater, and the properties thereof were also good.

In Example 3, a catalyst carrier was not used. However, by combining the following conditions: to decrease the polymerization temperature, to use an aliphatic hydrocarbon as a solvent, to decrease the stirring rotation number, and to carry out ultrasonic wave irradiation, the plane orientation index ratio became a high value that was 12.2.

In Comparative Example 1, since hydrogen was used in the polymerization process, the viscosity-average molecular weight became small. As a result, the tensile strength was reduced.

In Comparative Example 2, a mesoporous structure compound was used as a catalyst carrier, but the processing was not carried out in the air. In addition, the stirring rotation number was high, and ultrasonic wave irradiation was not carried out, either. As a result, the plane orientation index ratio and the difference in melting point were decreased, and the properties thereof were also insufficient.

In Comparative Example 3, since a mesoporous structure compound having a large pore size was used, the viscosity-average molecular weight became small, the ΔH value, the plane orientation index ratio, and the difference in melting point were decreased, and the properties thereof were also insufficient.

In Comparative Example 4, since a common Ziegler-Natta catalyst was used, the ΔH value, the plane orientation index ratio and the difference in melting point were decreased, and the properties thereof were also insufficient.

In Comparative Example 5, amorphous silica having no mesoporous structures was used as a catalyst carrier. In this case, the ΔH value, the plane orientation index ratio and the difference in melting point were decreased, and the properties thereof were also insufficient.

In Comparative Example 6, a mesoporous structure compound was used as a catalyst carrier, but the processing was not carried out in the air, an aromatic hydrocarbon was used as a solvent, the stirring rotation number was high, and ultrasonic wave irradiation was not carried out, either. As a result, the viscosity-average molecular weight became small, the ΔH, the plane orientation index ratio and the difference in melting point were decreased, and the properties thereof were also insufficient.

The ethylene polymer of the present invention has a high molecular weight and a high quantity of heat of fusion, and also has a low degree of entanglement of molecular chains in a higher-order structure. Accordingly, regardless of its high molecular weight, the present ethylene polymer can be stretched at a high ratio with a low tensile stress, and is excellent in terms of stretch processability. Moreover, since the molecular chains are highly oriented after completion of the stretching, a stretch-molded product having excellent mechanical strength can be obtained.

The disclosure of Japanese Patent Application No. 2014-205180 filed on Oct. 3, 2014, is incorporated in the present description by reference in its entirety.

In addition, all publications, patent applications and technical standards cited herein are incorporated in the present description by reference in their entirety, to such an extent that these publications, patent applications and technical standards are specifically and individually described herein.

INDUSTRIAL APPLICABILITY

Since the ethylene polymer of the present invention has a high molecular weight and a high quantity of heat of fusion, and also has a low degree of entanglement of molecular chains, a molded product with high strength can be obtained, in particular, when the present ethylene polymer is molded by a solid-phase stretching method. In addition, the present ethylene polymer can be stretch processed at a high speed without giving adverse effects on the mechanical properties of a stretch-molded product, and thus, it is also excellent in terms of productivity. Hence, the ethylene polymer of the present invention can be preferably used for intended uses in which molding is carried out by solid-phase stretching, for example, for intended uses such as ropes, nets, bulletproof and/or protective clothes, protective gloves, fiber-reinforced concrete products, and helmets.

We claim:

1. An ethylene polymer having a viscosity-average molecular weight (Mv) of 3,000,000 or more and 15,000,000 or less, wherein the quantity of heat of fusion ΔH measured by differential scanning calorimetry, of the ethylene polymer to which heat history at 110° C. for 6 hours has been given under a reduced pressure environment of 0.1 to 0.5 kPa, is 230 J/g or more and 293 J/g or less, and the plane orientation index ratio (b)/(a), between 200/110 plane orientation index (a) in an unprocessed ethylene polymer and 200/110 plane orientation index (b) in a sheet which has been subjected to press processing and rolling processing under the following conditions (1) to (3), is 10 or more:

(1) 3 g of the ethylene polymer is pressed using a press molding machine at 130° C. at 11 MPa for 10 minutes, (2) the resultant is cooled at 25° C. for 10 minutes, while maintaining the pressure at 11 MPa, and (3) the obtained press sheet is heated at 140° C. for 3 minutes, and the resulting sheet is then compressed using a rolling mill having a temperature of 130° C. and a feeding rate of the roll of 1 m/min, to result in a stretch ratio of 6.

2. The ethylene polymer according to claim 1, wherein the plane orientation index ratio (b)/(a) is 16 or more.

3. The ethylene polymer according to claim 1, wherein the difference in melting point ($T_{1b}$-$Tm_{1a}$), between the melting point ($Tm_{1a}$) of the unprocessed ethylene polymer by differential scanning calorimetry and the melting point ($Tm_{1b}$) of the sheet subjected to press processing and rolling processing under the conditions (1) to (3) by differential scanning calorimetry, is 3.0° C. or more.

4. A stretch-molded product obtained by the stretch molding of the ethylene polymer according to claim 1, wherein the stretch-molded product has a tensile strength of 3.0 GPa or more.

5. A method for producing the ethylene polymer according to claim 1, which comprises performing polymerization using a mixed solvent comprising 50% by mass or more of an aliphatic hydrocarbon.

6. A method for producing the ethylene polymer according to claim 1, which comprises performing a polymerization comprising applying an olefin polymerization catalyst comprising (A) a transition metal compound, and (C) at least one compound used as a co-catalyst which is selected from among (C-1) an organic metal compound, (C-2) an organic aluminum oxy compound, and (C-3) a compound reacting with (A) the transition metal compound to form an ion pair, wherein the olefin polymerization catalyst is irradiated with ultrasonic wave at 40 kHz or more before being added to a polymerization reactor.

7. The method according to claim 6, wherein the polymerization further comprises using a mixed solvent comprising 50% by mass or more of an aliphatic hydrocarbon.

8. A method for producing the ethylene polymer according to claim 1, which comprises performing a polymerization comprising allowing (A) a transition metal compound to come into contact with (B) a mesoporous structure compound to obtain a transition metal-containing mesoporous structure compound, and then using (C) at least one compound used as a co-catalyst which is selected from among (C-1) an organic metal compound, (C-2) an organic aluminum oxy compound, and (C-3) a compound reacting with (A) the transition metal compound to form an ion pair, and applying an olefin polymerization catalyst comprising the transition metal-containing mesoporous structure compound and the co-catalyst to perform polymerization using the olefin polymerization catalyst, wherein the olefin polymerization catalyst is irradiated with ultrasonic wave at 40 kHz or more before being adding to a polymerization reactor.

9. The method for producing an ethylene polymer according to claim 8, wherein the pore size of (B) the mesoporous structure compound is 1.5 nm or more and 10 nm or less.

10. The method according to claim 8, wherein the polymerization further comprises using a mixed solvent comprising 50% by mass or more of an aliphatic hydrocarbon.

11. A method for producing the ethylene polymer according to claim 1, which comprises performing a polymerization comprising
allowing (A) a transition metal compound to come into contact with (B) a mesoporous structure compound to produce a mixture, then
allowing the mixture to come into contact with a substance that modifies (A) the transition metal compound to obtain a transition metal-containing mesoporous structure compound, and then
using (C) at least one compound used as a co-catalyst which is selected from among (C-1) an organic metal compound, (C-2) an organic aluminum oxy compound, and (C-3) a compound reacting with (A) the transition metal compound to form an ion pair, and
applying an olefin polymerization catalyst comprising the transition metal-containing mesoporous structure compound and the co-catalyst to perform polymerization using the olefin polymerization catalyst,
wherein the olefin polymerization catalyst is irradiated with ultrasonic wave at 40 kHz or more before being added to a polymerization reactor.

12. The method according to claim 11, wherein the polymerization further comprises using a mixed solvent comprising 50% by mass or more of an aliphatic hydrocarbon.

13. A method for producing the ethylene polymer according to claim 1, which comprises allowing (A) a transition metal compound to come into contact with (B) a mesoporous structure compound, in which reactive points on the outer surfaces of mesopores have been inactivated, to obtain a transition metal-containing mesoporous structure compound, and then using (C) at least one compound used as a co-catalyst which is selected from among (C-1) an organic metal compound, (C-2) an organic aluminum oxy compound, and (C-3) a compound reacting with (A) the transition metal compound to form an ion pair, to perform polymerization using an olefin polymerization catalyst comprising the transition metal-containing mesoporous structure compound and the co-catalyst.

14. The method according to claim 13, wherein the polymerization further comprises using a mixed solvent comprising 50% by mass or more of an aliphatic hydrocarbon.

15. A method for producing a stretch-molded product, comprising compressing and stretching the ethylene polymer according to claim 1 under conditions that do not increase the temperature above the melting point of the ethylene polymer at any time point during the compressing and the stretching.

16. The method for producing a stretch-molded product according to claim 15, wherein the tensile strength of the obtained stretch-molded product is 3.0 GPa or more.

* * * * *